(12) United States Patent
Kobayashi et al.

(10) Patent No.: US 9,763,558 B2
(45) Date of Patent: Sep. 19, 2017

(54) ENDOSCOPE APPARATUS, METHOD FOR OPERATING ENDOSCOPE APPARATUS, AND INFORMATION STORAGE DEVICE

(71) Applicant: OLYMPUS CORPORATION, Tokyo (JP)

(72) Inventors: Naruyasu Kobayashi, Kawasaki (JP); Kazuhiro Takizawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 553 days.

(21) Appl. No.: 14/314,110

(22) Filed: Jun. 25, 2014

(65) Prior Publication Data

US 2015/0005575 A1 Jan. 1, 2015

(30) Foreign Application Priority Data

Jun. 27, 2013 (JP) .................................. 2013-134769

(51) Int. Cl.
*A61B 1/04* (2006.01)
*A61B 1/06* (2006.01)
(Continued)

(52) U.S. Cl.
CPC ...... *A61B 1/00009* (2013.01); *A61B 1/00193* (2013.01); *A61B 1/045* (2013.01);
(Continued)

(58) Field of Classification Search
CPC ..... A61B 1/00009; A61B 1/043; A61B 1/045; A61B 1/0638; A61B 1/00193;
(Continued)

(56) References Cited

U.S. PATENT DOCUMENTS 6,549,288 B1 * 4/2003 Migdal .................. G01B 11/25
356/601
6,825,884 B1 * 11/2004 Horiuchi .............. H04N 1/4074
348/222.1

(Continued)

FOREIGN PATENT DOCUMENTS

| JP | S59-069055 A | 4/1984 |
| JP | 62-161004 A | 7/1987 |
| JP | 2007-135756 A | 6/2007 |

OTHER PUBLICATIONS

Japanese Office Action dated Feb. 7, 2017 in Japanese Patent Application No. 2013-134769.

*Primary Examiner* — John P Leubecker
*Assistant Examiner* — Arnaldo Torres Diaz
(74) *Attorney, Agent, or Firm* — Scully, Scott, Murphy & Presser, P.C.

(57) ABSTRACT

An endoscope apparatus includes an endoscope that includes an imaging section that captures an object, and an illumination section that includes an irradiation port that illuminates the object, the imaging section and the illumination section being provided in an end section of the endoscope, a distance information acquisition section that acquires distance information about a distance from the end section of the endoscope to the object, a light distribution pattern determination section that determines a light distribution pattern of illumination light applied from the illumination section based on the acquired distance information, and a gradation correction section that performs a gradation correction process on a captured image acquired by the imaging section.

25 Claims, 15 Drawing Sheets

(51) Int. Cl.
*A61B 1/00* (2006.01)
*A61B 1/045* (2006.01)
*H04N 5/217* (2011.01)
*H04N 5/225* (2006.01)
*H04N 5/243* (2006.01)

(52) U.S. Cl.
CPC ........... *H04N 5/217* (2013.01); *H04N 5/2256* (2013.01); *H04N 5/243* (2013.01); *H04N 2005/2255* (2013.01)

(58) Field of Classification Search
CPC ........... H04N 2005/2255; H04N 5/217; H04N 5/2256; H04N 5/243; H04N 5/00; H04N 7/00; H04N 9/77–9/78; G02B 23/24; G02B 23/2415; G02B 23/2461; G02B 23/2469; G02B 26/02; G02B 26/004
See application file for complete search history.

(56) References Cited

U.S. PATENT DOCUMENTS

| | | | | |
|---|---|---|---|---|
| 7,258,663 | B2* | 8/2007 | Doguchi | A61B 1/00059 348/65 |
| 8,285,041 | B2* | 10/2012 | Toyoda | G06T 5/009 345/589 |
| 8,723,974 | B2* | 5/2014 | Suzuki | H04N 5/2355 348/218.1 |
| 8,831,372 | B2* | 9/2014 | Akiyama | G06T 5/002 382/261 |
| 9,149,175 | B2* | 10/2015 | Avni | A61B 1/00006 |
| 2006/0214121 | A1* | 9/2006 | Schrey | G01S 7/481 250/559.38 |
| 2007/0112247 | A1 | 5/2007 | Hirata | |
| 2009/0167908 | A1* | 7/2009 | Mori | A61B 1/00009 348/251 |
| 2010/0201795 | A1* | 8/2010 | Sato | A61B 1/00045 348/65 |
| 2012/0242812 | A1* | 9/2012 | Koizumi | A61B 1/00009 348/65 |
| 2014/0063229 | A1* | 3/2014 | Olsson | H04N 5/2252 348/84 |
| 2014/0184769 | A1* | 7/2014 | Ishihara | A61B 1/00009 348/68 |
| 2014/0228635 | A1* | 8/2014 | Tuliakov | A61B 1/06 600/109 |
| 2015/0124060 | A1* | 5/2015 | Hasegawa | G03B 35/08 348/47 |
| 2015/0374210 | A1* | 12/2015 | Durr | A61B 1/041 600/111 |

* cited by examiner

| 1.48 | 2.5 | 1.48 |
|------|------|------|
| 2.5 | 8.28 | 2.5 |
| 1.48 | 2.5 | 1.48 |

FIG. 9

| 0 | 0 | 0 |
|---|---|---|
| 0 | 1 | 0 |
| 0 | 0 | 0 |

FIG. 10

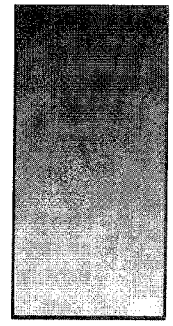

PATTERN 3
DISTANCE TO OBJECT DIFFERS
IN HORIZONTAL DIRECTION

EX.: VALUES OF AREAS ARE
IDENTICAL IN VERTICAL DIRECTION
120120120

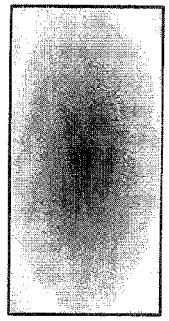

PATTERN 2
DISTANCE TO OBJECT DIFFERS
BETWEEN CENTER AND
PERIPHERAL AREA

EX.: VALUE OF ONE OR TWO
AREAS IS 1 (LONG DISTANCE),
AND VALUES OF REMAINING
AREAS ARE IDENTICAL
000010000

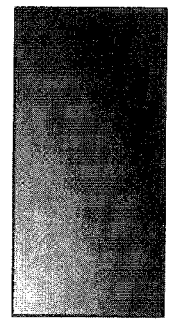

PATTERN 5
DISTANCE TO OBJECT DIFFERS
IN DIAGONAL DIRECTION

EX.: VALUES OF CENTER AREA
AND PERIPHERAL AREA ARE COMPARED
(WHEN VALUE OF CENTER AREA
IS AVERAGE VALUE)
002021211

PATTERN 1
DISTANCE TO OBJECT IS
ALMOST IDENTICAL OVER
ENTIRE AREA

EX.: NINE DIGITS ARE IDENTICAL
000000000
111111111
222222222

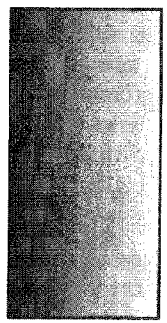

PATTERN 4
DISTANCE TO OBJECT DIFFERS
IN VERTICAL DIRECTION

EX.: VALUES OF AREAS ARE
IDENTICAL IN HORIZONTAL
DIRECTION
111222000

 RANGE IN WHICH DISTANCE TO OBJECT IS DETERMINED TO BE RELATIVELY LONG

 RANGE IN WHICH DISTANCE TO OBJECT IS DETERMINED TO BE RELATIVELY SHORT

| DISTANCE INFORMATION | LIGHT DISTRIBUTION PATTERN | | | | |
|---|---|---|---|---|---|
| | IRRADIATION PORT 12a / UPPER IRRADIATION PORT | IRRADIATION PORT 12b / RIGHT IRRADIATION PORT | IRRADIATION PORT 12c / LOWER IRRADIATION PORT | IRRADIATION PORT 12d / LEFT IRRADIATION PORT | IRRADIATION PORT 12e / CENTER IRRADIATION PORT |
| PATTERN 1 | IDENTICAL BRIGHTNESS | | | | |
| PATTERN 2 | DARK | DARK | DARK | DARK | BRIGHT |
| PATTERN 3 | IDENTICAL | BRIGHT | IDENTICAL | DARK | IDENTICAL |
| PATTERN 4 | BRIGHT | IDENTICAL | DARK | IDENTICAL | IDENTICAL |
| PATTERN 5 | DARK | BRIGHT | BRIGHT | DARK | IDENTICAL |

IRRADIATION RANGE OF IRRADIATION PORT 12b          IRRADIATION RANGE OF IRRADIATION PORT 12a

ENDOSCOPE APPARATUS, METHOD FOR OPERATING ENDOSCOPE APPARATUS, AND INFORMATION STORAGE DEVICE

Japanese Patent Application No. 2013-134769 filed on Jun. 27, 2013, is hereby incorporated by reference in its entirety.

BACKGROUND

The present invention relates to an endoscope apparatus, a method for operating an endoscope apparatus, an information storage device, and the like.

The main object of an electronic endoscope apparatus is an in vivo image, and external light does not reach the inside of the body. Therefore, it is necessary to apply illumination light to the object from the endoscope apparatus when acquiring a captured image using the endoscope apparatus. It is necessary to apply illumination light so that the observation area is captured at the correct exposure in order to improve the visibility of the captured image acquired by applying illumination light.

For example, JP-A-62-161004 discloses a method that ensures that the object is captured at the correct exposure. The method disclosed in JP-A-62-161004 detects distance data relating to the distance between the photoelectric sensor and the object, and controls the illumination intensity and the illumination direction of illumination light based on the distance data so that the object can always be observed under optimum illumination conditions.

JP-A-62-161004 mainly aims to implement pattern recognition of parts using a robot. On the other hand, the main object of endoscopic observation is to detect a lesion area. Specifically, endoscopic observation does not search an obvious object, differing from pattern matching. Therefore, since the object is the entire captured image, the entire image must be uniformly illuminated instead of optimizing the illumination conditions at one point within the image.

SUMMARY

According to one aspect of the invention, there is provided an endoscope apparatus comprising:

an endoscope that includes an imaging section that captures an object, and an illumination section that includes an irradiation port that illuminates the object, the imaging section and the illumination section being provided in an end section of the endoscope;

a distance information acquisition section that acquires distance information about a distance from the end section of the endoscope to the object;

a light distribution pattern determination section that determines a light distribution pattern of illumination light applied from the illumination section based on the acquired distance information; and a gradation correction section that performs a gradation correction process on a captured image acquired by the imaging section.

According to another aspect of the invention, there is provided a method for operating an endoscope apparatus that includes an endoscope, the endoscope including an imaging section that captures an object, and an illumination section that includes an irradiation port that illuminates the object, the imaging section and the illumination section being provided in an end section of the endoscope, the method comprising:

performing a distance information acquisition process that acquires distance information about a distance from the end section of the endoscope to the object;

performing a light distribution pattern determination process that determines a light distribution pattern of illumination light applied from the illumination section based on the acquired distance information; and performing a gradation correction process on a captured image acquired by the imaging section.

According to another aspect of the invention, there is provided a computer-readable storage device with an executable program stored thereon, the program operating an endoscope apparatus that includes an endoscope, the endoscope including an imaging section that captures an object, and an illumination section that includes an irradiation port that illuminates the object, the imaging section and the illumination section being provided in an end section of the endoscope, wherein the program instructs a computer to perform steps of:

acquiring distance information about a distance from the end section of the endoscope to the object;

determining a light distribution pattern of illumination light applied from the illumination section based on the acquired distance information; and performing a gradation correction process on a captured image acquired by the imaging section.

BRIEF DESCRIPTION OF THE DRAWINGS

FIG. 6 illustrates another example of distance information.

FIG. 7 illustrates an example of distance information that is divided into a plurality of areas.

FIG. 8 illustrates an example of average distance information about each area.

FIG. 9 illustrates an example of conversion results based on average distance information about each area and average distance information about the entire area.

FIG. 10 illustrates an example of distance information pattern classification.

FIG. 11 illustrates another example of distance information.

FIG. 12 illustrates an example of a light distribution pattern.

DESCRIPTION OF EXEMPLARY EMBODIMENTS

Figure 1:
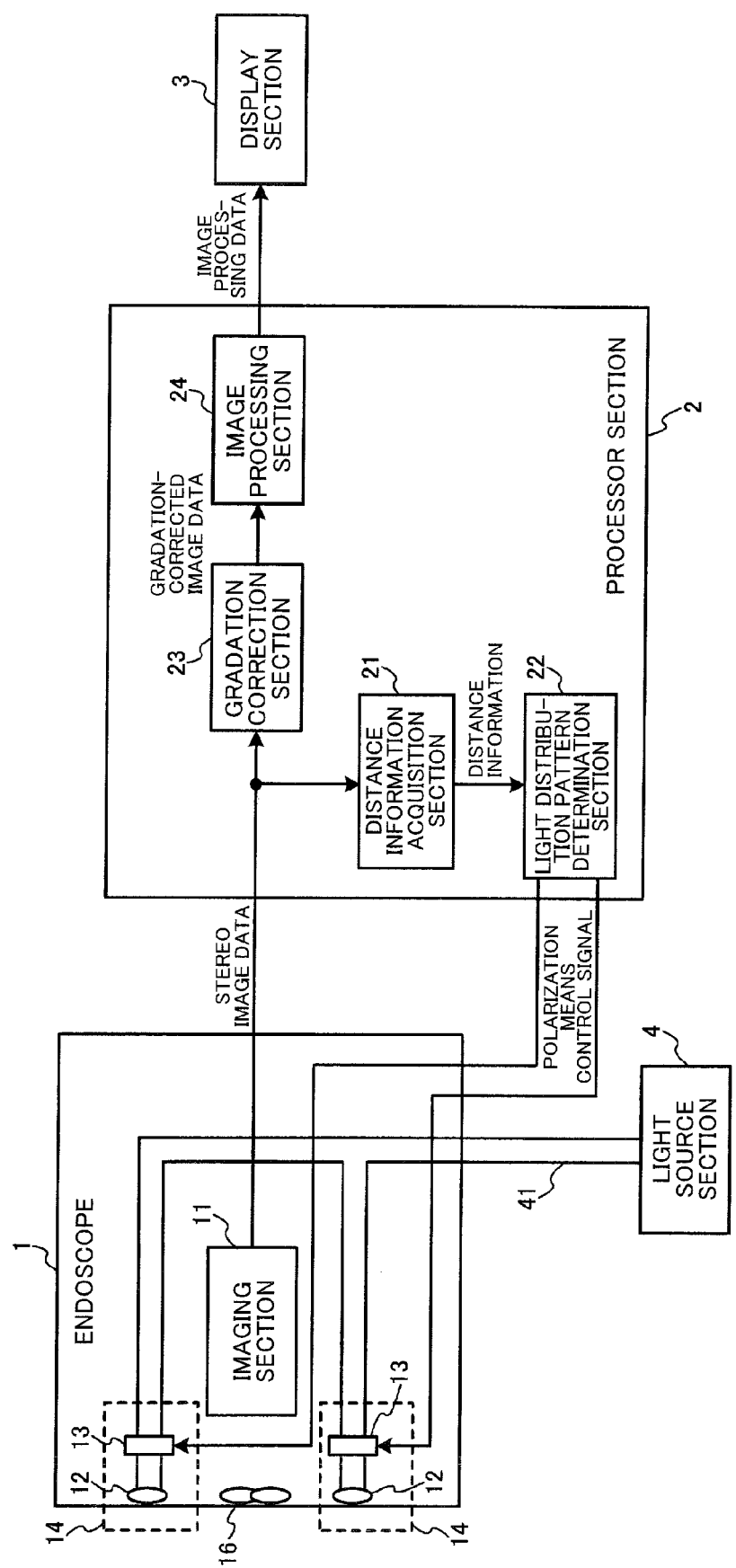
FIG. 1 illustrates a configuration example of an endoscope apparatus according to one embodiment of the invention.

According to one embodiment of the invention, there is provided an endoscope apparatus comprising:

an endoscope that includes an imaging section that captures an object, and an illumination section that includes an irradiation port that illuminates the object, the imaging section and the illumination section being provided in an end section of the endoscope;

a distance information acquisition section that acquires distance information about a distance from the end section of the endoscope to the object;

a light distribution pattern determination section that determines a light distribution pattern of illumination light applied from the illumination section based on the acquired distance information; and a gradation correction section that performs a gradation correction process on a captured image acquired by the imaging section.

According to another embodiment of the invention, there is provided a method for operating an endoscope apparatus that includes an endoscope, the endoscope including an imaging section that captures an object, and an illumination section that includes an irradiation port that illuminates the object, the imaging section and the illumination section being provided in an end section of the endoscope, the method comprising:

performing a distance information acquisition process that acquires distance information about a distance from the end section of the endoscope to the object;

performing a light distribution pattern determination process that determines a light distribution pattern of illumination light applied from the illumination section based on the acquired distance information; and performing a gradation correction process on a captured image acquired by the imaging section.

According to another embodiment of the invention, there is provided a computer-readable storage device with an executable program stored thereon, the program operating an endoscope apparatus that includes an endoscope, the endoscope including an imaging section that captures an object, and an illumination section that includes an irradiation port that illuminates the object, the imaging section and the illumination section being provided in an end section of the endoscope, wherein the program instructs a computer to perform steps of:

acquiring distance information about a distance from the end section of the endoscope to the object;

determining a light distribution pattern of illumination light applied from the illumination section based on the acquired distance information; and performing a gradation correction process on a captured image acquired by the imaging section.

Exemplary embodiments of the invention are described below. Note that the following exemplary embodiments do not in any way limit the scope of the invention laid out in the claims. Note also that all of the elements described in connection with the following exemplary embodiments should not necessarily be taken as essential elements of the invention.

1. Method

A method employed in connection with several exemplary embodiments of the invention is described below. When capturing an in vivo image using an endoscope apparatus, it is necessary to apply illumination light to the object from an illumination section of the endoscope apparatus since ambient light (e.g., sunlight) does not reach the object. In this case, if the intensity of light applied to the observation target object is too high, the object is captured too brightly within the captured image (e.g., blown out highlights occur due to too large a brightness value), and observation is hindered. If the intensity of light applied to the observation target object is too low, the object is captured too darkly within the captured image (e.g., blocked up shadows occur due to too small a brightness value), and observation is also hindered. Specifically, it is necessary to apply illumination light (irradiation light) so that the observation area is captured at the correct exposure.

However, when using irradiation light applied from the illumination section instead of ambient light (e.g., sunlight), the intensity of light that reaches the object varies to a large extent depending on the distance from the illumination section to the object. Specifically, an object that is situated close to the illumination section is captured brightly, and an object that is situated away from the illumination section is captured darkly. Therefore, it is effective to employ a method that implements correct exposure by controlling the illumination section based on distance information about the distance from the illumination section to the observation target object.

For example, JP-A-62-161004 discloses a method that detects distance data relating to the distance between the photoelectric sensor and the object, and controls the illumination intensity and the illumination direction of illumination light based on the distance data. However, JP-A-62-161004 aims to capture parts and the like using a robot. Therefore, the captured image may include an area other than the desired parts. However, the method disclosed in JP-A-62-161004 does not take account of the exposure in an area of the captured image other than the desired parts as long as the desired parts are captured at the correct exposure. On the other hand, it is difficult to clearly determine the attention area when capturing an image using an endoscope apparatus (e.g., a lesion area is searched by screening using an endoscope apparatus). Therefore, it is not effective to apply the method disclosed in JP-A-62-161004 that captures a specific object at the correct exposure to an endoscope apparatus in order to improve the visibility of the object within the captured image.

Figures 2, 3:
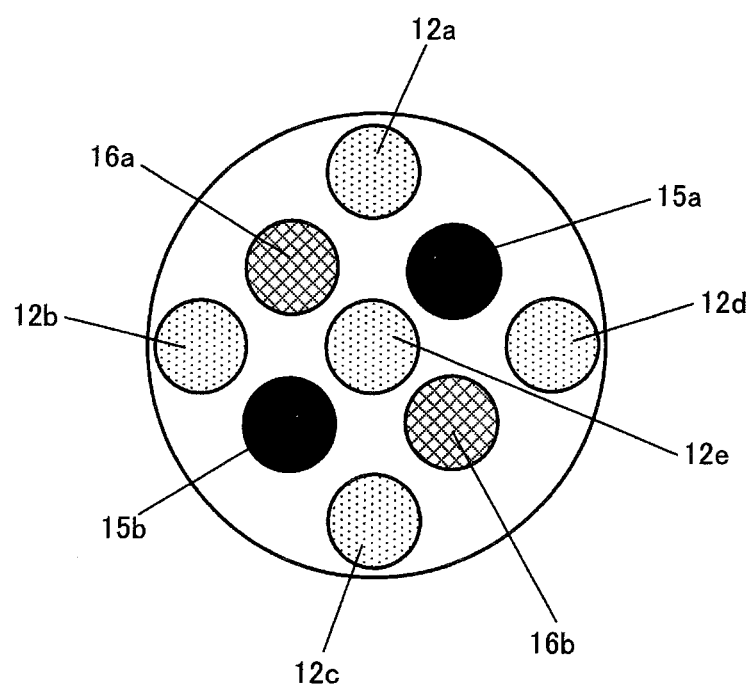
FIG. 2 illustrates an example in which distance information is divided into a plurality of areas.
FIG. 3 illustrates a configuration example of an end section of an endoscope apparatus.

In JP-A-62-161004, the imaging section (TV camera) and the illumination section (illumination device) need not necessarily be provided integrally (see FIG. 2 of JP-A-62-161004). The illumination direction of the illumination section can be changed using a driver device (illumination apparatus driver device) so that the desired object is captured at the correct exposure. On the other hand, the imaging section and the illumination section of the endoscope apparatus are provided to the endoscope (scope or endoscopic scope) that is inserted into the body of a patient, and it is necessary to implement a thin endoscope taking account of the burden imposed on the patient. Therefore, it is likely that the positional relationship between the imaging section and the illumination section is limited, or it is impossible to provide a driver section that changes the illumination direction of the illumination section. The method disclosed in JP-A-62-161004 is also not effective from this point of view.

Several aspects of the invention propose a method that determines a light distribution pattern based on distance information about the distance from the endoscope to the object, and applies illumination light according to the determined light distribution pattern. Note that the term "light distribution pattern" used herein refers to data that indicates the pattern of the intensity of irradiation light applied from the illumination section in each irradiation direction. For example, when the intensity of light applied to an object that is captured in the right area of the captured image, the intensity of light applied to an object that is captured in the left area of the captured image, and the intensity of light applied to an object that is captured in the center area of the captured image, can be defined when acquiring the captured image, information represented by "left-area light intensity, center-area light intensity, right-area light intensity" corresponds to the light distribution pattern.

For example, when the illumination section includes a plurality of irradiation ports that differ in illumination target area (see FIG. 3), the light distribution pattern is data that determines the intensity of light applied from each irradiation port. Specifically, when the illumination section includes five irradiation ports, the light distribution pattern is generated by combining five pieces of information that indicate the degree of irradiation light (e.g., information that indicates "identical", "dark", or "bright" with respect to a reference light intensity (see FIG. 12)). The light distribution pattern may be a pattern 1 (identical, identical, identical, identical, identical) or a pattern 2 (dark, dark, dark, dark, bright) illustrated in FIG. 12.

Although an example in which the illumination section includes a plurality of irradiation ports is described below, the method that controls the intensity of irradiation light in each direction is not limited thereto. For example, the intensity of irradiation light in each direction may be controlled using an optical system (e.g., lens or filter). In such a case, the light distribution pattern also refers to data that indicates the pattern of the intensity of irradiation light applied from the illumination section in each irradiation direction.

Several aspects of the invention also propose a method that performs a gradation correction process on the acquired captured image in addition to applying irradiation light based on the light distribution pattern. The configuration of the illumination section of the endoscope apparatus tends to be simplified in order to implement a thin endoscope. Therefore, it is difficult to set a complex light distribution pattern, and a simple light distribution pattern that specifies the light intensity in three directions or five directions is used, for example. On the other hand, tissue has a complex and irregular shape due to folds or the like, and the distance information (distance map in a narrow sense) that indicates the distance from the endoscope to each object tends to become complex. Therefore, an area that cannot be captured at the correct exposure may occur when using only the light distribution pattern.

When using a plurality of irradiation ports, the intensity of irradiation light applied from a given irradiation port is high in the front direction, and decreases in a direction away from the front direction. Therefore, the object may become significantly dark when irradiation light applied from all of the irradiation ports does not sufficiently reach the object, or may become significantly bright when irradiation light applied from a plurality of irradiation ports reaches the object. In this case, it may be difficult to implement correct exposure using only the light distribution pattern. For example, when the end section of the endoscope includes an objective lens 16 that corresponds to the imaging section, and two irradiation ports 12a and 12b (see FIG. 18A), the irradiation port 12a illuminates the right area of the captured image, and the irradiation port 12b illuminates the left area of the captured image (see FIG. 18B). In this case, the intensity of irradiation light applied from each irradiation port is high at the center of the irradiation range (circular area), and decreases as the distance from the center of the irradiation range increases. Therefore, it may be difficult to implement correct exposure using the light distribution pattern in the shaded area that is situated away from the center of each irradiation range, for example.

Specifically, since an area that cannot be captured at the correct exposure may occur when using the illumination section having a simple configuration and a simple light distribution pattern, such an area is dealt with using the gradation correction process.

Several embodiments of the invention relate to an endoscope apparatus including an endoscope 1 that includes an imaging section 11 that captures an object, and an illumination section 14 that includes an irradiation port that illuminates the object, the imaging section 11 and the illumination section 14 being provided in an end section of the endoscope 1, a distance information acquisition section 21 that acquires distance information about the distance from the end section of the endoscope 1 to the object, a light distribution pattern determination section 22 that determines a light distribution pattern of illumination light applied from the illumination section 14 based on the acquired distance information, and a gradation correction section 23 that performs a gradation correction process on a captured image acquired by the imaging section 11 (see FIG. 1).

According to this configuration, it is possible to adjust the difference in exposure state corresponding to distance by controlling the illumination section using the light distribution pattern, and implement correct exposure in an area that cannot be covered by the illumination section by performing the gradation correction process on the captured image. This makes it possible to implement the desired exposure state, and improve the visibility of the object, differing from JP-A-62-161004, when implementing an endoscope apparatus that is required to implement correct exposure over a wide range of the captured image (the entire captured image in a narrow sense).

A first embodiment and a second embodiment of the invention are described below. The first embodiment illustrates a basic method that controls the illumination section using the light distribution pattern, and performs the gradation correction process. The second embodiment illustrates a method that utilizes a gain map generated by the gradation correction process for another process. The gain map may be used for a noise reduction process, a light distribution pattern determination process, a light source light intensity control process, and the like.

2. First Embodiment

The first embodiment is described below. A system configuration example of an endoscope apparatus according to the first embodiment, a light distribution pattern determination process based on the distance information, and modifications are described below in this order.

2.1 System Configuration Example

FIG. 1 illustrates a system configuration example of the endoscope apparatus according to the first embodiment. The endoscope apparatus according to the first embodiment includes an endoscope 1, a processor section 2, a display section 3, and a light source section 4. Note that the configuration of the endoscope apparatus and the configuration of each section of the endoscope apparatus are not limited to the configuration illustrated in FIG. 1. Various modifications may be made, such as omitting some of the elements illustrated in FIG. 1, or adding other elements.

The endoscope 1 includes an imaging section 11 that is implemented by a CCD sensor or the like, and an illumination section 14 that applies light emitted from the light source to the object. The illumination section 14 includes an irradiation port 12 from which light emitted from the light source is applied, and a polarization means 13 for adjusting the intensity of light applied from the irradiation port 12. In the first embodiment, the imaging section 11 includes two image sensors (e.g., CCD), and outputs a right image and a left image (stereo image) respectively captured by the two image sensors as an image of the object.

The processor section 2 performs image processing that converts image signals from the endoscope 1 into data suitable for observation. The display section 3 is a device (e.g., CRT or liquid crystal monitor) that can display a movie (moving image). The light source section 4 includes a light source (e.g., halogen lamp or LED). Light emitted from the light source section 4 is applied from the end of the endoscope 1 through a light guide cable 41 (e.g., optical fiber).

The details of the processor section 2 are described below. As illustrated in FIG. 1, the processor section 2 includes a distance information acquisition section 21, a light distribution pattern determination section 22, a gradation correction section 23, and an image processing section 24.

The distance information acquisition section 21 acquires the distance information that indicates the distance from the end of the endoscope 1 to the object (not illustrated in FIG. 1) from the stereo image data acquired from the imaging section 11. The distance information may be a distance map in which a distance value (i.e., a signal value that indicates the distance to the object corresponding to each pixel) is stored on a pixel basis, or may be another information that indicates distance.

The distance information acquisition section 21 compares the right image and the left image included in the acquired stereo image data to calculate the distance information, and outputs the distance information to the light distribution pattern determination section 22. The distance information acquisition section 21 may acquire the distance information by applying a stereo matching technique or the like. For example, the distance information acquisition section 21 performs matching calculations on the left image (reference image) included in the captured stereo image and a local area of the right image along an epipolar line that passes through the attention pixel positioned at the center of a local area of the left image to calculate the position at which the maximum correlation is obtained as a parallax. The distance information acquisition section 21 converts the calculated parallax into the distance in the direction Z to acquire the distance information (distance map in a narrow sense). Various stereo matching techniques that may be used to acquire the distance information using the stereo image are known in the art, and an arbitrary technique among such stereo matching techniques may be applied. Therefore, further description of the distance information acquisition process is omitted.

The light distribution pattern determination section 22 determines the light distribution pattern of the endoscope 1 from the calculated distance information, and outputs a polarization means control signal. The details of the light distribution pattern determination process based on the distance information are described later.

The gradation correction section 23 performs an adaptive gradation correction process (e.g., a correction process that utilizes a retinex algorithm) on the stereo image data acquired from the imaging section 11. For example, the gradation correction section 23 may generate a gain map corresponding to each pixel of the captured image by setting a large gain value (gain) to a pixel having a small brightness value, and setting a small gain value (gain) to a pixel having a large brightness value, and perform a gain-up process using the gain value represented by the gain map. In this case, it is possible to improve the visibility of the object (i.e., an area of the captured image having a small brightness value) for which sufficient brightness cannot be achieved by controlling the illumination section 14 using the light distribution pattern. The gradation correction process (e.g., retinex algorithm) is widely known in the art, and further description thereof is omitted.

The image processing section 24 performs image processing for generating an image suitable for observation, an image size conversion process for displaying an image on the display section 3, and the like on the stereo image data subjected to image processing by the gradation correction section 23.

2.2 Light Distribution Pattern Determination Process

The light distribution pattern determination process is described below. The light distribution pattern determination section 22 generates the distance map based on the distance information received from the distance information acquisition section 21, and performs a short distance/long distance detection process on the captured image using the values included in the distance map. The light distribution pattern determination section 22 determines the light distribution pattern based on the detection results. A specific operation of the light distribution pattern determination section 22 is described below.

The light distribution pattern determination section 22 generates the distance map from the received distance information, and divides the distance map into nine areas. The light distribution pattern determination section 22 then calculates average distance information about each area. The light distribution pattern determination section 22 calculates the average distance information about each area using a normal method (e.g., a method that divides total distance information about each area by a total distance information count). Note that the term "total distance information" used herein refers to the sum of the distance values included in each area, and the term "total distance information count" used herein refers to the number of distance values included in each area (e.g., corresponding to the pixel count of each area of the distance map).

The light distribution pattern determination section 22 calculates the average distance information about the entire area, compares the average distance information about each area with the average distance information about the entire area, and converts the distance of each area into a distance-related value (0 (short distance), 1 (long distance), or 2 (identical distance)). The distance-related value of each area is combined according to an area number and a digit position determined in advance to generate nine-digit distance data. The number of each area illustrated in FIG. 2 is used as the area number, for example.

The light distribution pattern determination section 22 stores information about the number and the positions of irradiation ports of the illumination section 14 in advance, and selects the light distribution pattern based on a combination of the stored information and the calculated distance data.

The light distribution pattern selection method is described below using a specific example. FIG. 3 illustrates a configuration example of the end of the endoscope 1. In FIGS. 3, 12a to 12e are irradiation ports, 15a and 15b are forceps ports for passing a procedure tool, and 16a and 16b are objective lenses for capturing an image.

Figure 4:
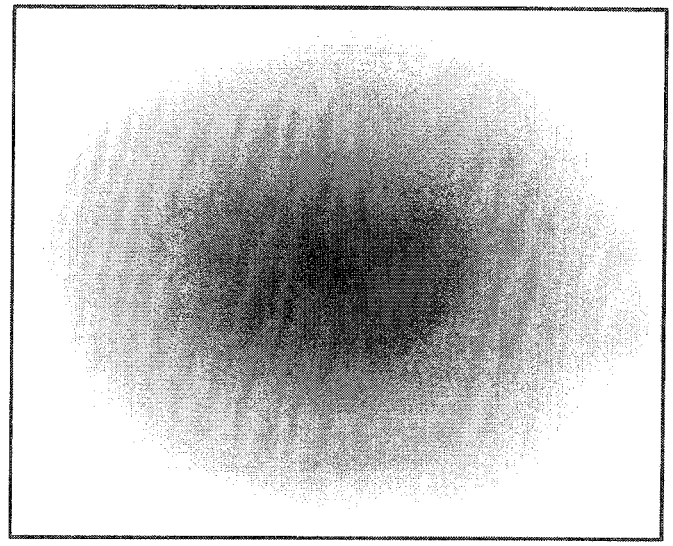
FIG. 4 illustrates an example of distance information.
Figure 5A:
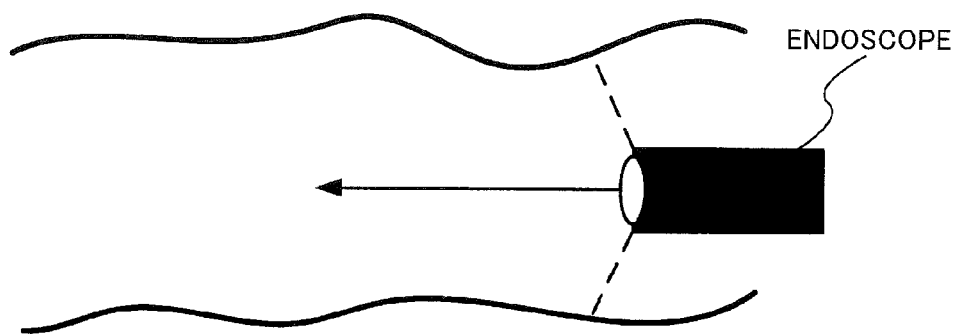
FIGS. 5A to 5C are views illustrating the relative positional relationship between an endoscope and an object in a typical observation state using an endoscope apparatus.

When a lumen (e.g., gullet or large intestine) is observed using the endoscope 1, the distance information is calculated from the stereo image data as illustrated in FIG. 4. Since the endoscope 1 and the wall surface of the lumen (object) have a positional relationship as illustrated in FIG. 5A when the lumen is observed using the endoscope 1, the distance to the object that is situated in the direction of the optical axis of the imaging section 11 is long, and the distance to the object that is situated in a direction away from the direction of the optical axis of the imaging section 11 is short. The object situated in the direction of the optical axis of the imaging section 11 is normally captured in the center area of the captured image, and the object situated in a direction away from the direction of the optical axis of the imaging section 11 is normally captured in the peripheral area of the captured image. Therefore, the distance information is calculated as illustrated in FIG. 4. In FIG. 4, the brightness decreases as the distance to the object increases, and increases as the distance to the object decreases.

Figure 6:
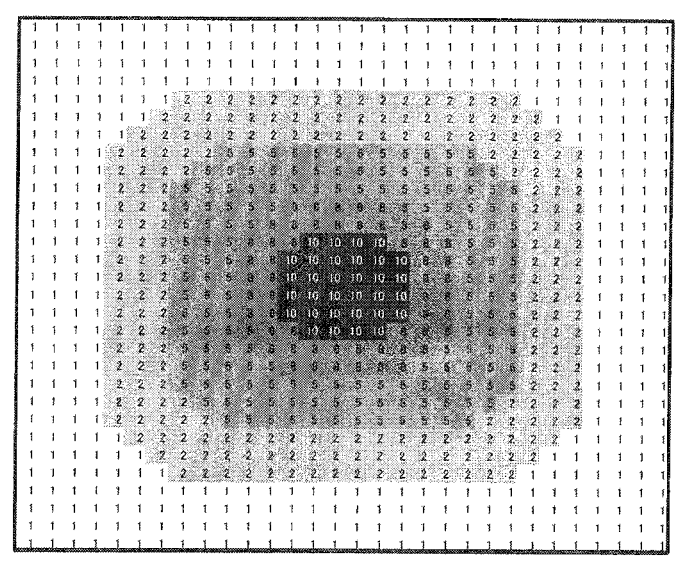

The distance information acquisition section 21 outputs the distance information illustrated in FIG. 4 to the light distribution pattern determination section 22 using the received stereo image data and a stereo matching technique or the like. The light distribution pattern determination section 22 generates the distance map illustrated in FIG. 6 from the received distance information. In FIG. 6, the distance value is set in the range of 1 to 10. Note that the distance value is not limited thereto. In FIG. 6, 1 indicates that the object is situated at the shortest distance, and 10 indicates that the object is situated at the farthest distance, for example. FIG. 6 illustrates an example corresponding to the distance information illustrated in FIG. 4. Most of the distance values in the center area are 8, 9, or 10 (long distance), and most of the distance values in the peripheral area are 1 or 2 (short distance).

Although an example has been described above in which the distance information acquisition section 21 acquires the information illustrated in FIG. 4, and the light distribution pattern determination section 22 calculates the distance map illustrated in FIG. 6 that is information having a granularity smaller than that of the information illustrated in FIG. 4, the configuration is not limited thereto. For example, the light distribution pattern determination section 22 may perform the following process using the information illustrated in FIG. 4. Alternatively, the distance information acquisition section 21 may acquire the information illustrated in FIG. 6 when detailed distance information is unnecessary. Note that the term "distance information" used herein includes both the information illustrated in FIG. 4 and the information illustrated in FIG. 6.

Figures 7, 8, 9:
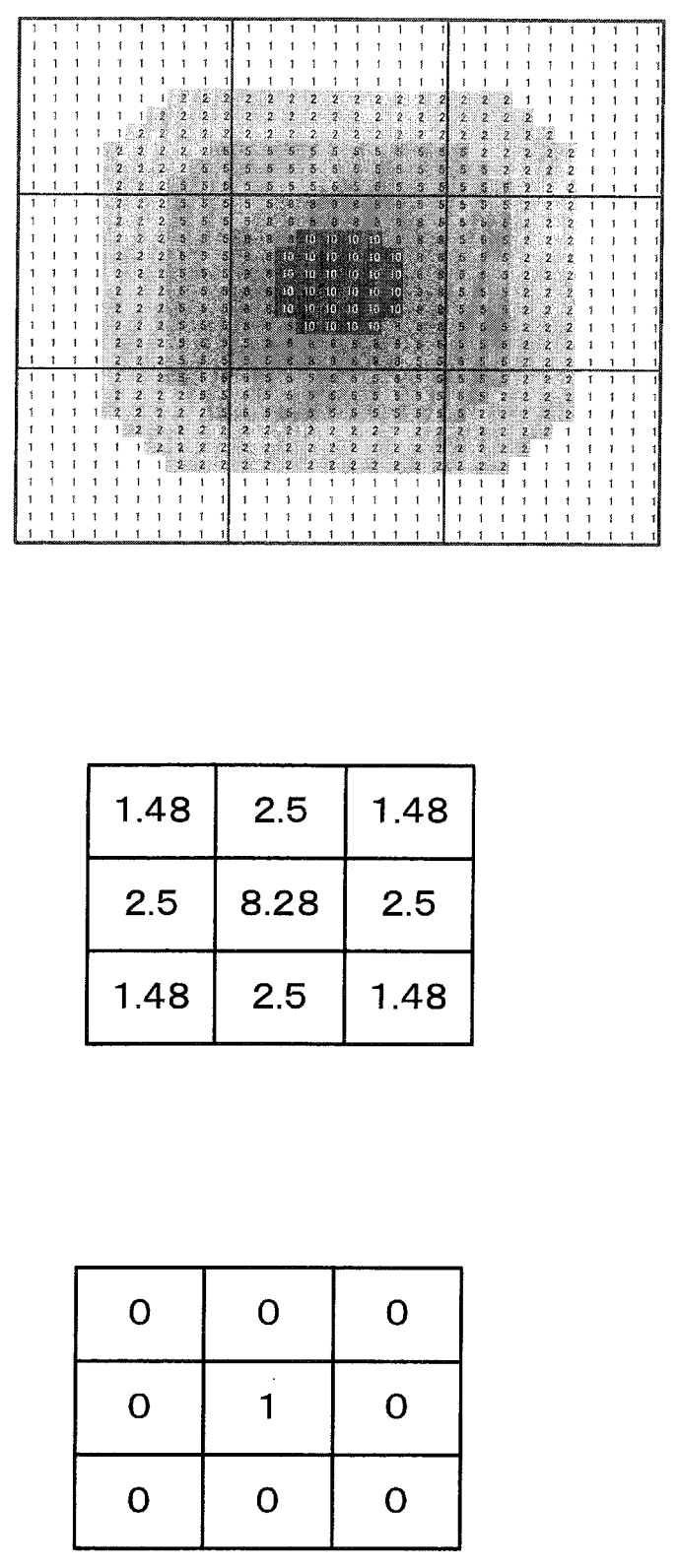

The light distribution pattern determination section 22 calculates the average distance information about the entire area using the calculated distance information. The light distribution pattern determination section 22 divides the distance information into nine areas (see FIG. 7), and calculates the average distance information about each area. FIG. 8 illustrates an example of the calculated average distance information.

The light distribution pattern determination section 22 then compares the average distance information about the entire area with the average distance information about each area. The light distribution pattern determination section 22 determines that the average distance information about each of the areas 1 to 4 and 6 to 9 is smaller than the average distance information about the entire area (i.e., the distance to the object is short), and determines that the distance-related value of each of the areas 1 to 4 and 6 to 9 is 0 (short distance). The light distribution pattern determination section 22 determines that the average distance information about the area 5 is larger than the average distance information about the entire area (i.e., the distance to the object is long), and determines that the distance-related value of the area 5 is 1 (long distance). FIG. 9 illustrates the results obtained by converting the comparison results into the distance-related values.

The light distribution pattern determination section 22 converts the distance-related values into a nine-digit distance value in the order of the area number. For example, the distance-related values illustrated in FIG. 6 are converted into a nine-digit distance value (information) "000010000". The light distribution pattern determination section 22 then determines a light distribution pattern table using the nine-digit value corresponding to the number and the positions of irradiation ports of the imaging section.

The number of pieces of distance information corresponding to the nine-digit values is about 20,000 (i.e., the ninth power of 3). However, it is unnecessary to actually take account of such a large number of pieces of distance information. This is because the observation state using the endoscope can be represented by one of several typical examples. FIG. 10 illustrates such typical examples (pattern 1 to pattern 5). The pattern 1 represents an observation state in which the endoscope is situated directly opposite to a wall surface (see FIG. 5B). In this case, the distance to the object situated in the direction of the optical axis differs to only a small extent from the distance to the object situated in a direction away from the direction of the optical axis. Therefore, the distance to the object is almost identical over the entire area (see the pattern 1) in the observation state illustrated in FIG. 5B. When the object is observed in the direction along a lumen (see FIG. 5A), the distance to the object situated in the direction of the optical axis (i.e., situated at the center) is long, and the distance to the object situated in a direction away from the direction of the optical axis (i.e., situated in the peripheral area) is short (see the pattern 2). Therefore, the area 5 has a large distance value, and the remaining areas have an identical distance value that is smaller than that of the area 5 (see FIGS. 4 and 10 (see the pattern 2)).

Figure 5B:
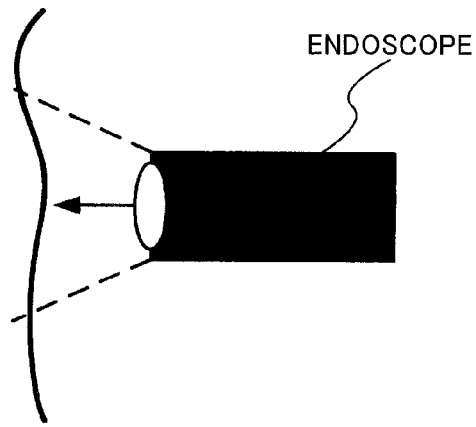
Figure 5C:
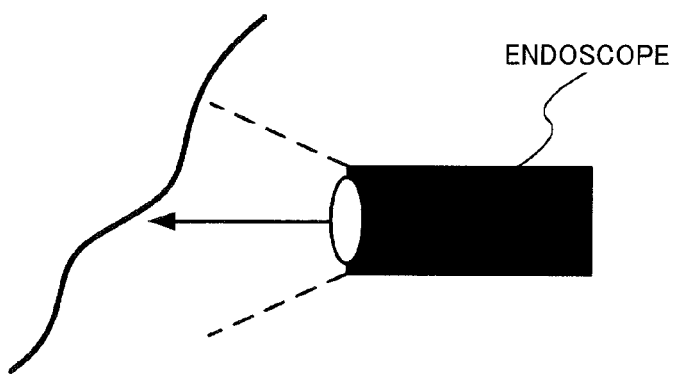
Figure 11:
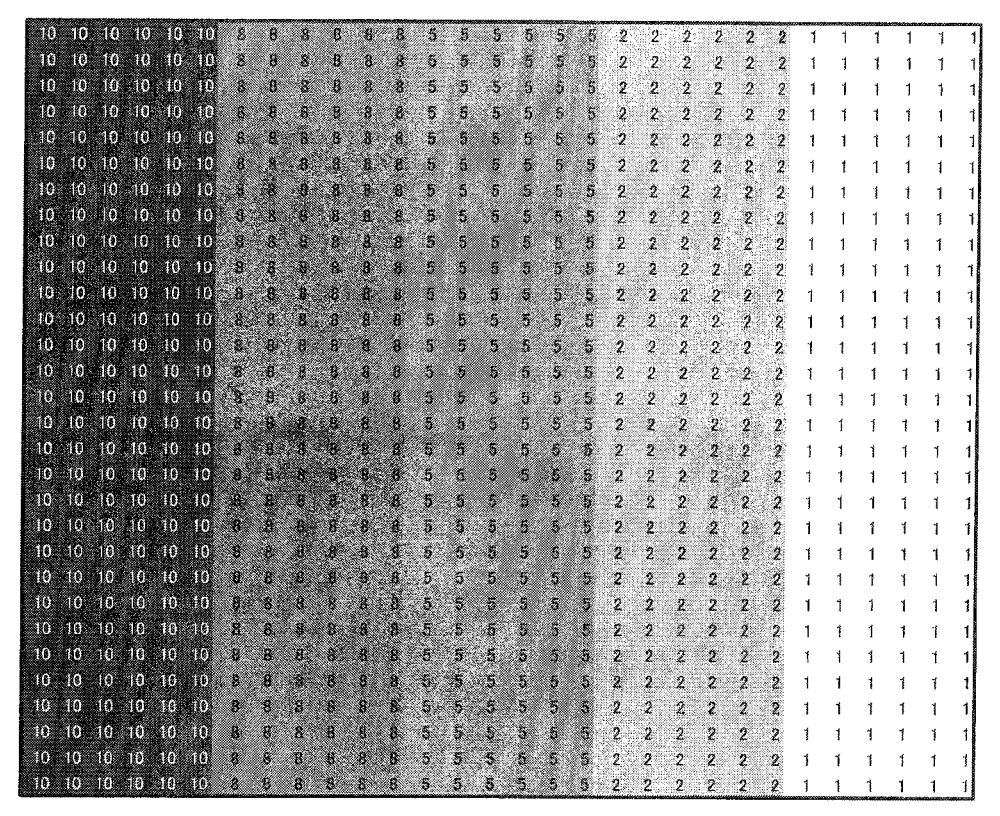

An observation state other than those illustrated in FIGS. 5A and 5B may be an intermediate observation state between the observation state illustrated in FIG. 5A and the observation state illustrated in FIG. 5B (i.e., an observation state in which the endoscope is situated diagonally to a wall surface (see FIG. 5C)). The observation states illustrated in FIGS. 5A to 5C cover typical observation states using the endoscope apparatus. Since an observation state in which the endoscope is situated diagonally to a wall surface is classified into a case where the distance to the object differs in the captured image in the horizontal direction, a case where the distance to the object differs in the captured image in the vertical direction, and a case where the distance to the object differs in the captured image in the diagonal direction (i.e., the direction from the upper left to the lower right, or the direction from the upper right to the lower left), the patterns 3 to 5 are provided. The pattern 3 represents an observation state in which the distance values are identical in the vertical direction, but differ in the horizontal direction (see FIG. 11). The pattern 4 represents an observation state in which the distance values are identical in the horizontal direction, but differ in the vertical direction. The pattern 5 represents an observation state in which the peripheral area includes an area in which the distance to the object is short (e.g., the area 1 in the example illustrated in FIG. 10), an area in which the distance to the object is farthest (e.g., the area 9), and an area in which the distance to the object is medium (e.g., the areas 3 and 7), and the average distance value of the peripheral area is close to that of the center area (e.g., the area 5).

The light distribution pattern determination section 22 determines the pattern that corresponds to the acquired distance information based on the features of each of the patterns 1 to 5. For example, the light distribution pattern determination section 22 determines that the acquired distance information falls under the pattern 2 when the fifth digit that corresponds to the center area is 1 (long distance), and the remaining digits are 0 (short distance) or 2 (identical distance). The light distribution pattern determination section 22 determines that the acquired distance information falls under the pattern 3 when the first digit, the fourth digit, and the seventh digit that correspond to the left side are 1 (long distance), and the second digit and the third digit that correspond to the right side are 2 (identical distance) or 0 (short distance).

The light distribution pattern determination section 22 determines the light distribution pattern that corresponds to the pattern corresponding to the distance information based on the determination result. FIG. 12 illustrates the relationship between the pattern corresponding to the distance information and the light distribution pattern when the end of the endoscope 1 is configured as illustrated in FIG. 3 (i.e., when the illumination section 14 includes five irradiation ports (upper irradiation port, lower irradiation port, right irradiation port, left irradiation port, and center irradiation port).

The light distribution pattern is basically determined so that the intensity of irradiation light is increased corresponding to an object that is situated at a long distance, and is decreased corresponding to an object that is situated at a short distance. Therefore, when the distance information falls under the pattern 1, the intensity of irradiation light applied from each irradiation port may be set to be equal to the reference light intensity.

When the distance to the object is short in the peripheral area, and is long in the center area (e.g., when the nine-digit value is "000010000") (see the pattern 2), the light distribution pattern is selected so that the intensity of irradiation light applied from the irradiation ports 12a to 12d is decreased in order to decrease the brightness of the peripheral area, and the intensity of irradiation light applied from the irradiation port 12e is increased in order to increase the brightness of the center area.

When the distance information falls under the pattern 3, and the distance to the object is short in the left area, and is long in the right area, the light distribution pattern is selected so that the intensity of irradiation light applied from the irradiation port 12d is decreased in order to decrease the brightness of the left area, the intensity of irradiation light applied from the irradiation port 12b is increased in order to increase the brightness of the right area, and the intensity of irradiation light applied from the remaining irradiation ports is set to be equal to the reference light intensity. When the distance information falls under the pattern 3, and the distance to the object is long in the left area, and is short in the right area, differing from the example illustrated in FIG. 10, the light distribution pattern is selected so that the intensity of irradiation light applied from the irradiation port 12b is decreased, and the intensity of irradiation light applied from the irradiation port 12d is increased. This also applies to the case where the distance information falls under the pattern 4 or 5. Specifically, it is necessary to select the light distribution pattern corresponding to the bright area and the dark area.

The light distribution pattern determination section 22 outputs the polarization means control signal to each polarization means 13 (e.g., five polarization means 13a to 13e when five irradiation ports 12a to 12e are provided) of the endoscope based on the selected light distribution pattern to adjust the intensity of irradiation light applied from each irradiation port.

Since the positional relationship between the irradiation ports 12a to 12e and the objective lenses 16a and 16b provided to the end section of the endoscope 1 (see FIG. 3) is constant even when the position of the endoscope 1 has changed during observation, it is possible to determine the light distribution pattern corresponding directly to the position of the acquired stereo image data.

The light distribution pattern may be determined when the distance information corresponding to one frame has been calculated. However, since the body of the subject may be damaged when a frame delay has occurred when operating the endoscope apparatus, it is necessary to avoid a frame delay as much as possible. Therefore, the distance information in the current frame may be estimated using a frame correlation technique (e.g., a technique that calculates the difference from the distance information (map) in the preceding frame).

Since the intensity of irradiation light applied from the irradiation ports 12a to 12e of the endoscope 1 can be adjusted corresponding to the distance to the object based on the light distribution pattern determination process performed by the light distribution pattern determination section 22, it is possible to uniformly illuminate the object within the observation field of view.

2.3 Modifications

Various modifications may be made of the first embodiment. Although an example has been described above in which the irradiation ports (12a to 12e) of the endoscope 1 are provided at the five positions illustrated in FIG. 3, the number of irradiation ports is not limited to five. It is possible to implement finer control by increasing the number of irradiation ports. A fine light intensity control process may not be implemented when the number of irradiation ports is reduced. However, since the gradation correction section 23 can compensate for a decrease in fineness of the light intensity (distribution) control process, a significant deterioration in performance does not occur. Moreover, a thin endoscope 1 can be implemented by reducing the number of irradiation ports.

Although FIG. 1 illustrates an example in which the gradation correction section 23 is provided in the first stage of the processor section 2, the configuration (i.e., the order of connection) is not limited thereto. The gradation correction section 23 may perform the correction process after image processing has been performed.

Figure 13:
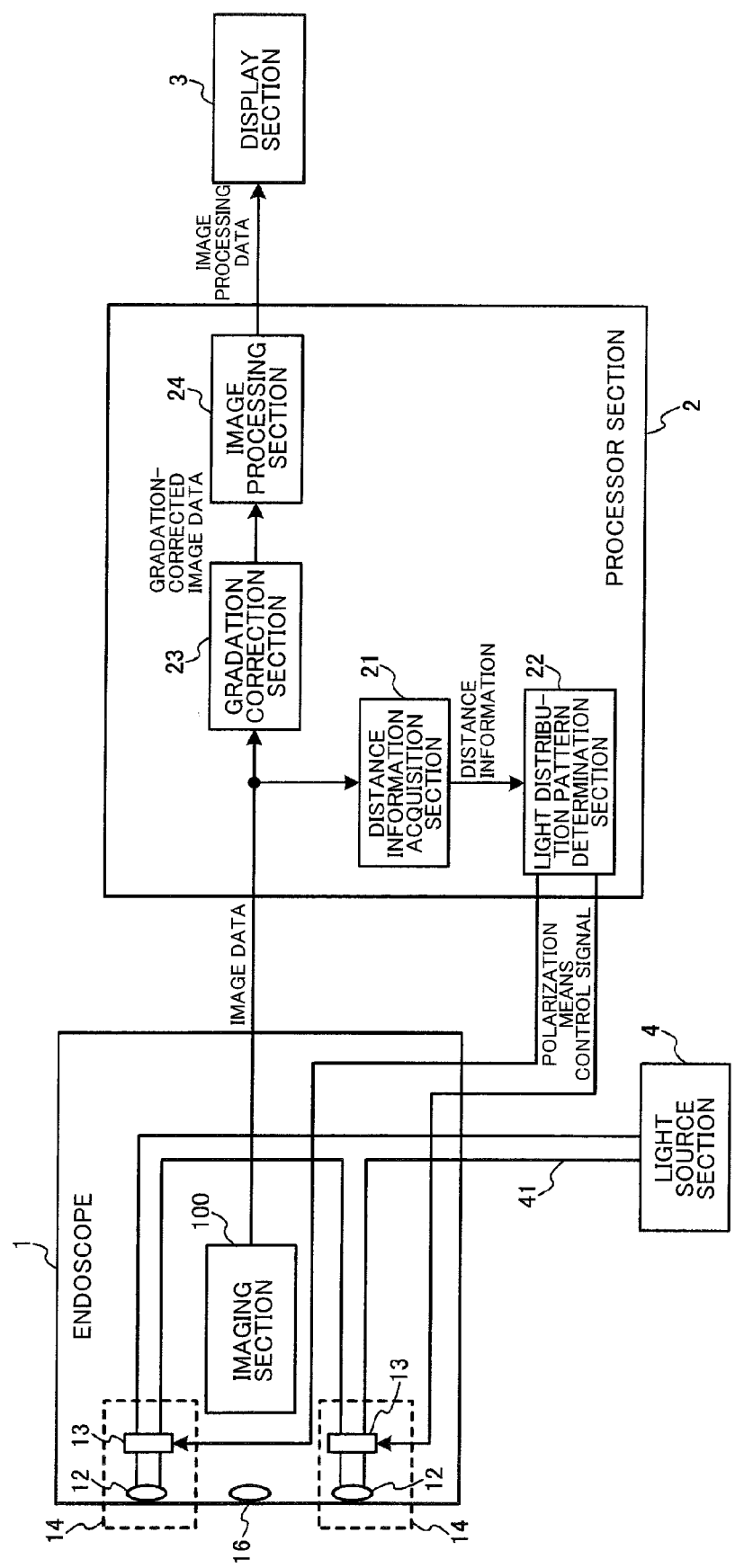
FIG. 13 illustrates another configuration example of an endoscope apparatus according to one embodiment of the invention.

The distance information may be acquired in various ways. For example, the endoscope apparatus according to the first embodiment may have the configuration illustrated in FIG. 13. In FIG. 13, the imaging section 11 is a single imager, and the image data is monaural image data. In this case, a brightness signal included in image data 101 is used as an alternative (alternative data) to the distance information. Specifically, a dark image is determined to be a long-distance image, and a bright image is determined to be a short-distance image. In this case, it is considered that the process may be affected the color of the object, and the accuracy of the distance information that can be estimated may decrease as compared with the case of using a stereo matching technique. However, it is possible to reduce the cost of the endoscope 1, for example.

Figure 14:
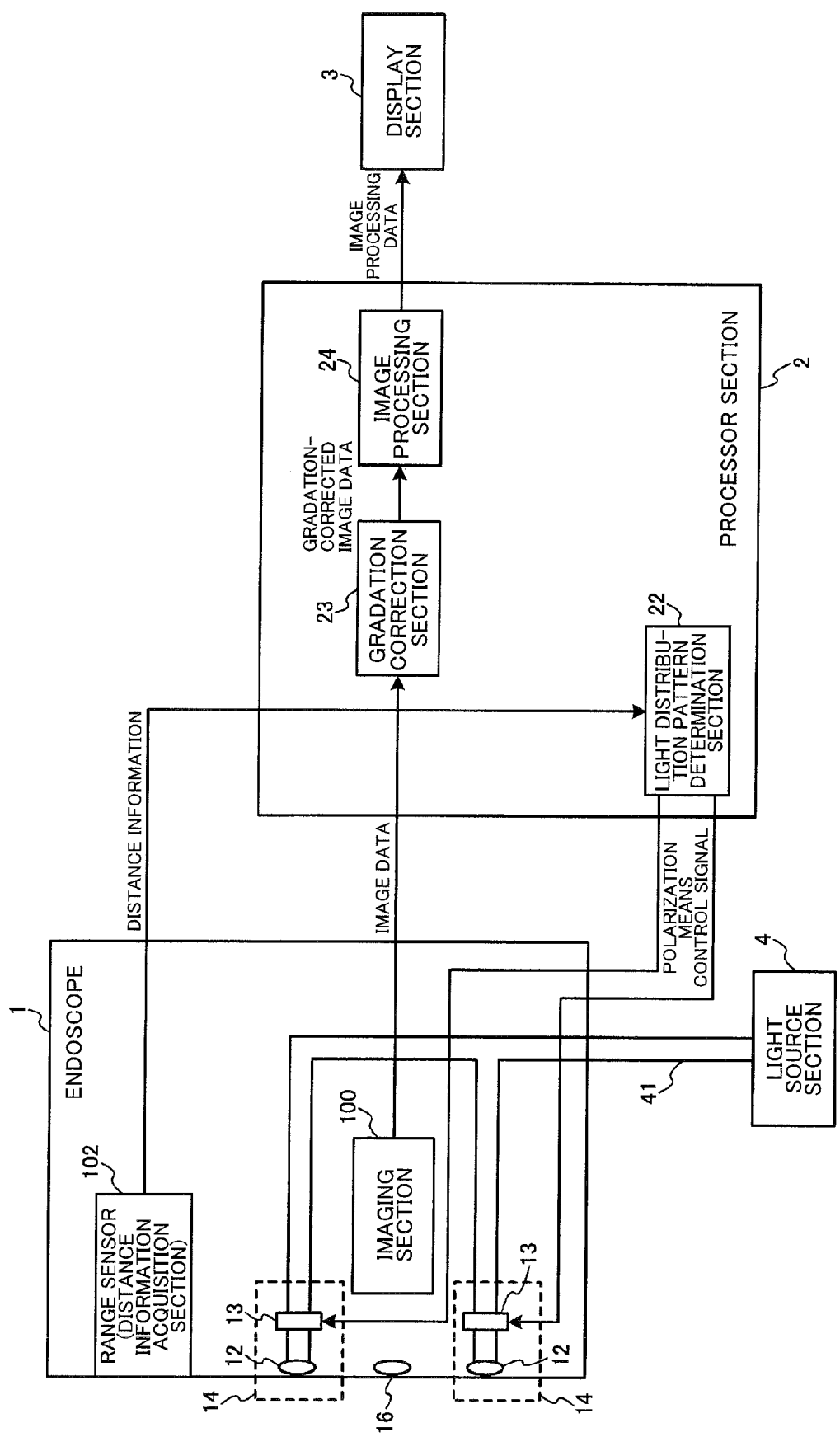
FIG. 14 illustrates another configuration example of an endoscope apparatus according to one embodiment of the invention.

The distance information may be acquired using a range sensor. In this case, the endoscope apparatus may have the configuration illustrated in FIG. 14. In FIG. 14, a range sensor 102 is provided to the end section of the endoscope 1, and the distance information is acquired directly from the range sensor 102. Although it is necessary to provide a space for providing the range sensor 102 when employing the configuration illustrated in FIG. 14, it is possible to acquire accurate distance information.

2.4 Specific Example of First Embodiment

According to the first embodiment, the endoscope apparatus includes the endoscope 1 that includes the imaging section 11 that captures an object, and the illumination section 14 that includes the irradiation port 12 that illuminates the object, the imaging section 11 and the illumination section 14 being provided in the end section of the endoscope 1, the distance information acquisition section 21 that acquires the distance information about the distance from the end section of the endoscope 1 to the object, the light distribution pattern determination section 22 that determines the light distribution pattern of illumination light applied from the illumination section 14 based on the acquired distance information, and the gradation correction section 23 that performs the gradation correction process on the captured image acquired by the imaging section 11 (see FIG. 1).

The distance information is information that indicates the distance from the endoscope 1 to the object. Since the distance information is used to determine the light distribution pattern of illumination light emitted from the illumination section 14, the distance information in a narrow sense is information that indicates the distance from the irradiation port 12 provided to the endoscope 1 to the object. The distance information may be a distance map in which a value that indicates the distance to the object corresponding to each pixel is stored on a pixel basis, for example. The distance information may be the information illustrated in FIG. 4, 6, or 11, for example. The light distribution pattern is data that indicates the pattern of the intensity of irradiation light applied from the illumination section 14 in each irradiation direction. The light distribution pattern may be the information illustrated in FIG. 12, for example.

According to the above configuration, since the light distribution pattern can be determined based on the distance information, it is possible to absorb the difference in brightness corresponding to the distance to the object, and implement correct exposure over a wide range (area) of the captured image. The above configuration is particularly useful for an apparatus that applies irradiation light without using ambient light (e.g., endoscope apparatus) since a change in brightness occurs to a large extent depending on the distance to the object. Moreover, it is possible to control the intensity of irradiation light applied from the illumination section 14 in each irradiation direction (e.g., the front direction, the vertical direction, and the horizontal direction when employing the configuration illustrated in FIG. 3) by utilizing the light distribution pattern. When the irradiation direction (front direction in a narrow sense) of the illumination section is mechanically changed as disclosed in JP-A-62-161004, light is not sufficiently applied in a direction other than the irradiation direction. In contrast, it is possible to apply light having an intensity that can implement correct exposure to a wide area (e.g., an area corresponding to the entire captured image) by utilizing the method according to the first embodiment. According to the first embodiment, since the gradation correction process is used in combination with the process that controls the illumination section based on the light distribution pattern, it is possible to deal with a variation in brightness (e.g., a situation in which the shaded area in FIG. 18B becomes dark) or the like that may occur when the illumination section 14 has a simple configuration (see FIG. 18A), and improve the visibility of the object, for example.

The illumination section 14 may include two or more irradiation ports (e.g., irradiation ports 12a to 12e) (see FIG. 3 or 18A), and the light distribution pattern determination section 22 may determine information that adjusts the intensity of illumination light applied from each of the two or more irradiation ports to be the light distribution pattern based on the distance information.

This makes it possible to implement the method according to the first embodiment by utilizing the illumination section 14 that includes a plurality of irradiation ports. Since the object brightness distribution changes in various ways (see the example of the pattern of the distance information illustrated in FIG. 10), the method according to the first embodiment is required to have versatility to appropriately deal with such various situations. Therefore, it is preferable that the illumination section 14 be configured so that the intensity of illumination light applied in each irradiation direction can be controlled. Such a configuration may be easily implemented by providing a plurality of irradiation ports corresponding to the respective irradiation directions. In this case, the light distribution pattern determined by the light distribution pattern determination section 22 is information that adjusts (determines) the intensity of illumination light applied from each irradiation port among the plurality of irradiation ports. Specifically, the intensity of illumination light applied from each irradiation port is controlled by controlling the polarization means 13 according to the determined light distribution pattern.

The illumination section 14 may include a first irradiation port that applies a first illumination light to the object that is captured in a first area of the captured image as the illumination light, and a second irradiation port that applies a second illumination light to the object that is captured in a second area of the captured image as the illumination light, the second area differing from the first area. The light distribution pattern determination section 22 may determine information that adjusts the intensity of the first illumination light applied from the first irradiation port and the intensity of the second illumination light applied from the second irradiation port to be the light distribution pattern based on the distance information.

Figure 18A:
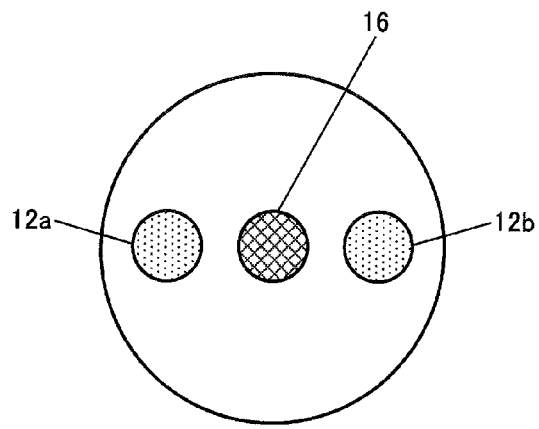
FIG. 18A illustrates another example of an end section of an endoscope.
Figure 18B:
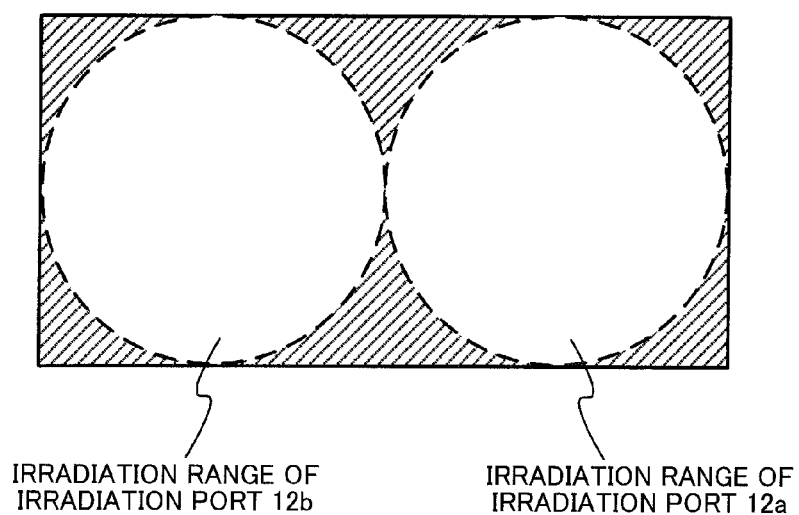
FIG. 18B illustrates an example of an irradiation range of each irradiation port within a captured image.

The first area may be a circular area that is drawn on the right side of the captured image illustrated in FIG. 18B, and the second area may be a circular area that is drawn on the left side of the captured image illustrated in FIG. 18B. Note that the expression "the second area differing from the first area" means that the first area does not coincide with the second area. Specifically, the captured image may include an overlapping area that is included in both the first area and the second area.

The illumination section 14 may include a first irradiation port that is provided to the end section of the endoscope 1 in a first direction with respect to the imaging section 11, and applies a first illumination light as the illumination light, and a second irradiation port that is provided to the end section of the endoscope 1 in a second direction with respect to the imaging section 11, and applies a second illumination light as the illumination light, the second direction differing from the first direction. In this case, the light distribution pattern determination section 22 may also determine information that adjusts the intensity of the first illumination light applied from the first irradiation port and the intensity of the second illumination light applied from the second irradiation port to be the light distribution pattern based on the distance information.

The first direction and the second direction refer to directions that differ from each other, and extend along a plane that is perpendicular to the endoscope 1 when the endoscope 1 is observed in a plan view. For example, FIGS. 3 and 18A are plan views illustrating the endoscope 1. The first direction corresponds to the rightward direction in FIG. 18A, and the second direction corresponds to the leftward direction in FIG. 18A, for example.

This makes it possible to link each irradiation port to each irradiation direction of the illumination section 14. For example, it is possible to set the intensity of light applied in a first irradiation direction to a first light intensity, and set the intensity of light applied in a second irradiation direction to a second light intensity by controlling the intensity of light applied from each irradiation port.

The imaging section 11 may include a plurality of viewpoints (see the objective lens 16 illustrated in FIG. 1), and acquire a plurality of captured images that respectively correspond to the plurality of viewpoints. The distance information acquisition section 21 may acquire the distance information based on parallax information obtained from the plurality of captured images acquired by the imaging section 11.

This makes it possible to acquire the distance information through a stereo matching process. In this case, it is necessary to provide a configuration for acquiring a stereo image (e.g., two objective lenses 16 illustrated in FIG. 1). However, it is unnecessary to provide a configuration other than the imaging section 11 in order to acquire the distance information. For example, since an endoscope apparatus or the like that displays a three-dimensional image uses a stereo image when generating a display image, it is possible to utilize the stereo image when acquiring the distance information for implementing the light distribution pattern determination process. This makes it possible to implement an endoscope apparatus using an efficient configuration.

The distance information acquisition section 21 may acquire the distance information from a measurement device (e.g., the range sensor 102 illustrated in FIG. 14) that measures distance.

This makes it possible to acquire the distance information using a ranging device such as a range sensor. In this case, the processing load is reduced as compared with the case of using the stereo matching process although it is necessary to provide a special device. When using the stereo matching process, the accuracy of the parallax information and the distance information acquired based on the parallax information may deteriorate when the contrast of the image is low, for example. On the other hand, it is possible to eliminate the effects of the image when using the range sensor.

The first embodiment may be applied to a method for operating an endoscope apparatus (or a method for controlling an endoscope apparatus, or an image processing method) that includes an endoscope that includes an imaging section that captures an object, and an illumination section that includes an irradiation port that illuminates the object, the imaging section and the illumination section being provided in an end section of the endoscope, the method including performing a distance information acquisition process that acquires distance information about the distance from the end section of the endoscope to the object, performing a light distribution pattern determination process that determines a light distribution pattern of illumination light applied from the illumination section based on the acquired distance information, and performing a gradation correction process on the captured image acquired by the imaging section.

Note that part or most of the processes performed by the endoscope apparatus and the like according to the first embodiment may be implemented by a program. In this case, the endoscope apparatus and the like according to the first embodiment are implemented by causing a processor (e.g., CPU) to execute a program. Specifically, a program stored in a non-transitory information storage device is read, and executed by a processor (e.g., CPU). The information storage device (computer-readable device) stores a program, data, and the like. The function of the information storage device may be implemented by an optical disk (e.g., DVD or CD), a hard disk drive (HDD), a memory (e.g., memory card or ROM), or the like. The processor (e.g., CPU) performs various processes according to the first embodiment based on the program (data) stored in the information storage device. Specifically, a program that causes a computer (i.e., a device including an operation section, a processing section, a storage section, and an output section) to function as each section according to the first embodiment (i.e., a program that causes a computer to execute the process implemented by each section) is stored in the information storage device.

The endoscope apparatus and the like according to the first embodiment may include a processor and a memory. The processor may be a central processing unit (CPU), for example. Note that the processor is not limited to a CPU. Various types of processors such as a graphics processing unit (GPU) and a digital signal processor (DSP) may also be used. The processor may be a hardware circuit that includes an application-specific integrated circuit (ASIC). The memory stores a computer-readable instruction. Each section of the endoscope apparatus and the like according to the first embodiment is implemented by causing the processor to execute the instruction. The memory may be a semiconductor memory (e.g., SRAM or DRAM), a register, a hard disk, or the like. The instruction may be an instruction included in an instruction set of a program, or may be an instruction that causes a hardware circuit of the processor to operate.

3. Second Embodiment

The second embodiment is described below. The second embodiment relates to a method in which the gain map calculated by the gradation correction section 23 is used for another process. The gain map is information that is generated by setting a large gain value to a pixel having a small brightness value, and setting a small gain value to a pixel having a large brightness value, and determines the gain-up process performed on the captured image. The gain map may be used for a noise reduction process, the light distribution pattern determination process, a light source light intensity control process, and the like.

3.1 Noise Reduction Process that Utilizes Gain Map

Figure 15:
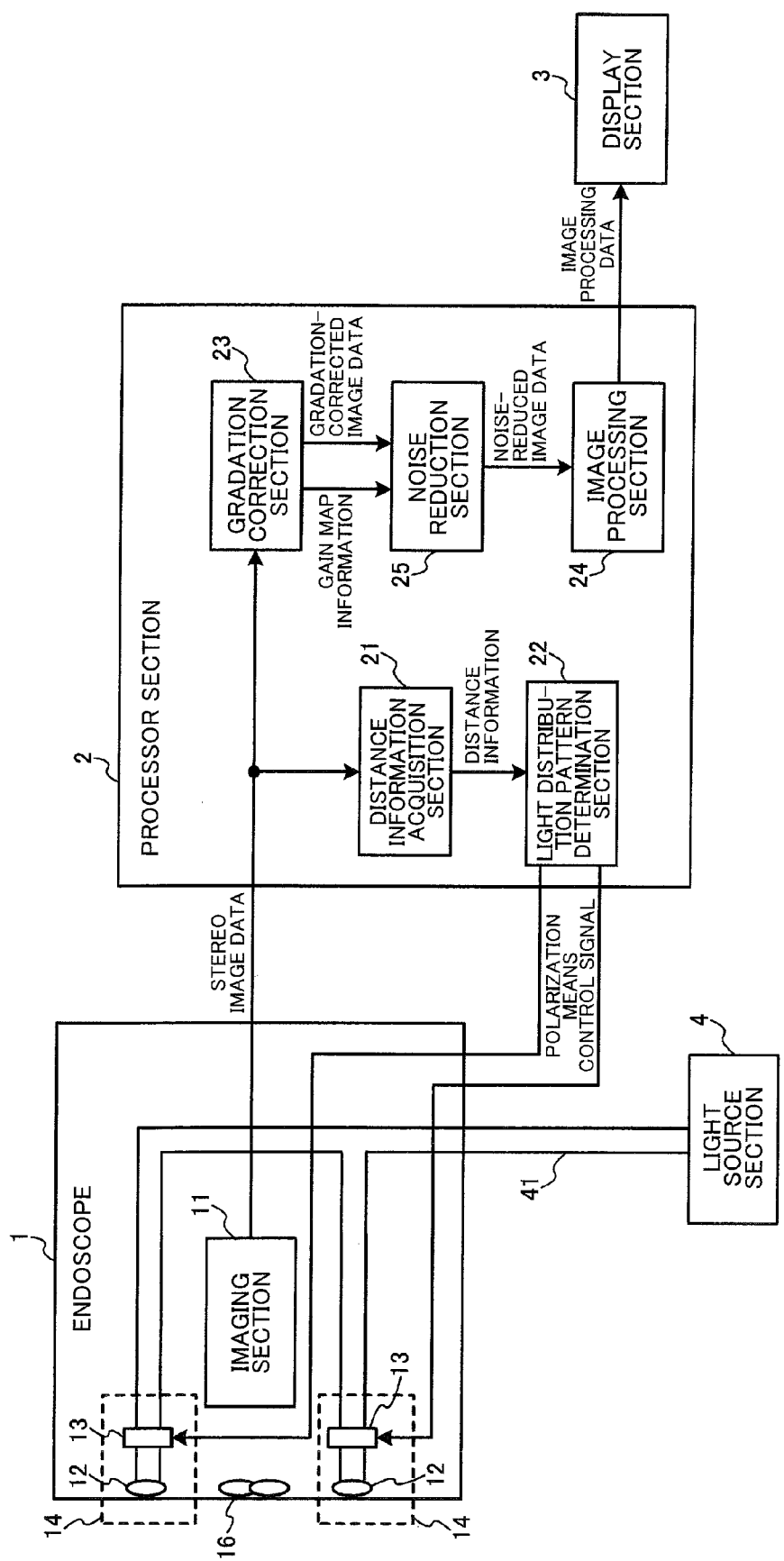
FIG. 15 illustrates another configuration example of an endoscope apparatus according to one embodiment of the invention.

FIG. 15 illustrates a system configuration example of an endoscope apparatus according to the second embodiment. Note that an element having the same function as that of the corresponding element described above in connection with the first embodiment is indicated by the corresponding reference sign, and description thereof is omitted. The processor section 2 according to the second embodiment includes a noise reduction section 25 in addition to the elements described above in connection with the first embodiment. The noise reduction section 25 includes a mechanism that reduces random noise superimposed on the stereo image data.

The gradation correction section 23 according to the second embodiment calculates the gain map that specifies the gain that is set to each area of the image, and performs the gradation correction process. The gradation correction section 23 outputs gain map information about the gain map to the noise reduction section 25.

The noise reduction section 25 compares each gain value included in the received gain map information with a given threshold value, and classifies each pixel into a plurality of areas depending on whether or not the gain value is within the range of each threshold value. The noise reduction section 25 determines the noise reduction level (i.e., the degree of the noise reduction process) on an area basis, and performs the noise reduction process. For example, the noise reduction section 25 increases the noise reduction level corresponding to an area having a large gain value. The amount of noise normally increases as the gain increases. However, since the noise reduction level is increased corresponding to an area having a large gain value, an increase in the amount of noise can be suppressed. Specifically, the quality of the entire image is improved by performing the noise reduction process using the gain map (i.e., changing the noise reduction level corresponding to the gain).

The image processing section 24 performs a given process on the received noise-reduced image data in the same manner as in the first embodiment.

Although an example has been described above in which the noise reduction section 25 that performs the noise reduction process is additionally provided, the image processing section 24 may perform the noise reduction process instead of the noise reduction section 25 (i.e., the noise reduction section 25 may not be provided).

3.2 Light Intensity Control Process that Utilizes Gain Map

Figure 16:
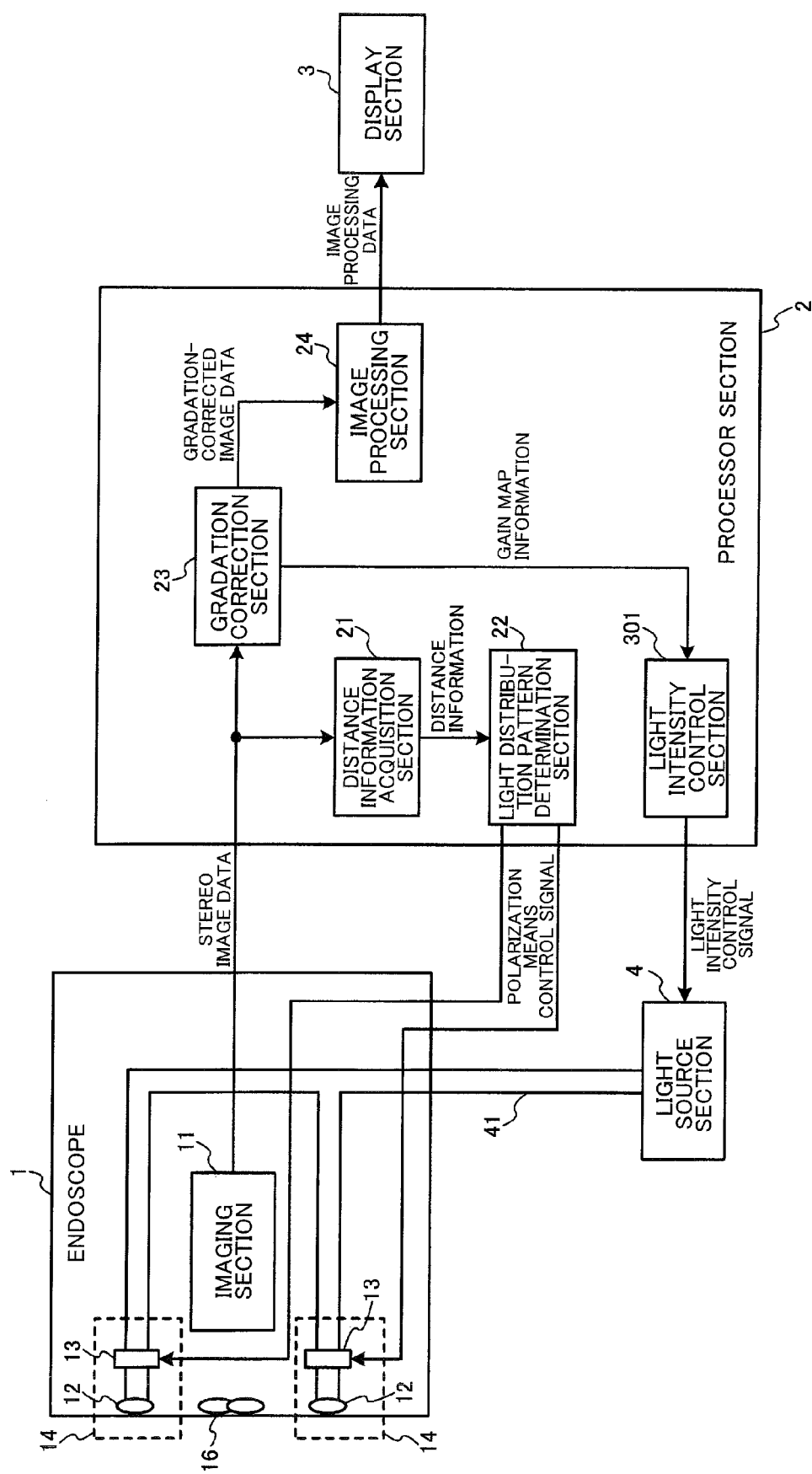
FIG. 16 illustrates yet another configuration example of an endoscope apparatus according to one embodiment of the invention.

The process that utilizes the gain map information is not limited to the noise reduction process. FIG. 16 illustrates a system configuration example of the endoscope apparatus when a light intensity control process is performed using the gain map.

In FIG. 16, the gradation correction section 23 outputs a light intensity control signal 303 to a light intensity control section 301 that controls the amount of light emitted from the light source section 4. The gradation correction section 23 determines the gain value included in the gain map calculated by the gradation correction process, and outputs the light intensity control signal to the light intensity control section 301 when the ratio of an area in which the gain value exceeds a given threshold value has exceeded a given ratio, the light intensity control signal increasing the intensity of illumination light in the subsequent frame to some extent (about 5 to 10%). Note that the intensity of illumination light is returned to the original value when the stereo image data in the subsequent frame is too bright, and blown out highlights may occur.

Since an increase in the amount of noise may occur due to multiplication of a gain through image processing, it is undesirable to apply an excessive gain. Since the gain value increases when the stereo image data is too dark, an increase in gain value can be prevented by increasing the brightness of the shooting environment. According to the second embodiment, since the light intensity is increased when the ratio of an area in which the gain value exceeds a given threshold value is large (i.e., when the amount of noise is expected to increase through image processing), the gain value can be reduced, and an unnecessary increase in the amount of noise can be prevented.

3.3 Light Distribution Pattern Determination Process that Utilizes Gain Map

The light distribution pattern determination process may be performed using the gain map information. As described above in connection with the light intensity control process that utilizes the gain map, it is considered that an area in which the gain value is large is an area in which the light intensity is insufficient, and it is considered that an area in which the gain value is small is an area in which the light intensity is sufficient.

In the first embodiment, the light distribution pattern is determined based on the distance information. Specifically, the intensity of light applied to the object is estimated based on the distance information, and the illumination light control process that compensates for brightness is performed using the estimation results. The expression "compensates for brightness" used herein refers to a process that increases the light intensity in an area in which it is estimated that the light intensity is insufficient, and decreases the light intensity in an area in which it is estimated that the light intensity is sufficient. Specifically, when the light intensity can be estimated from the gain map, it is possible to perform the light distribution pattern determination process that compensates for brightness based on the gain map in the same manner as in the case of using the distance information.

For example, the gain map may be classified in the same manner as the distance information (see FIG. 10), the pattern that corresponds to the gain map may be determined, and the light distribution pattern that corresponds to the pattern corresponding to the gain map may be determined.

Note that the pattern that corresponds to the distance information and the pattern that corresponds to the gain map may be determined independently, and the light distribution pattern may be determined based on a combination of the respective determination results. Alternatively, classification may be performed using both the distance information and the gain map as parameters. The light distribution pattern determination process that utilizes the distance information and the gain map may be implemented in various other ways.

3.4 Supplementary Explanation of Gain Map

The gain value applied to each pixel is relatively determined during the gradation correction process based on the relationship with the pixel value (e.g., brightness value) of another pixel within the image, for example. Specifically, the gain map (i.e., a set of the gain values applied to each pixel) is generated after an image has been generated.

Figure 17A:
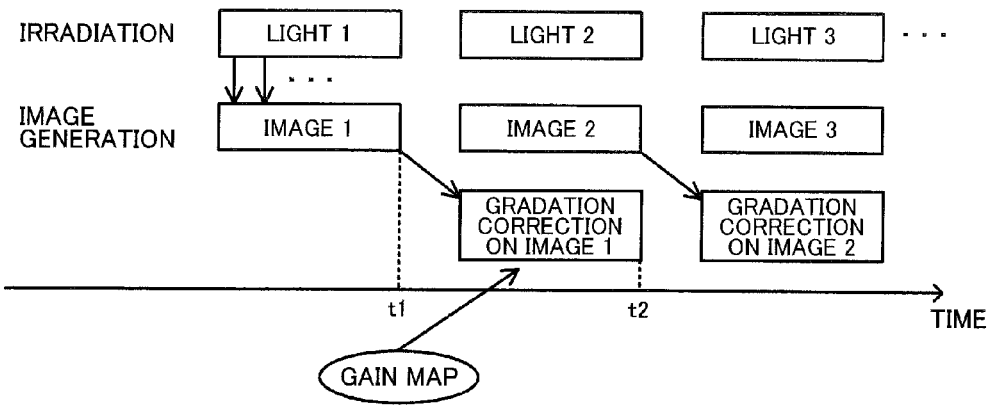
FIGS. 17A to 17C are timing charts of a process that utilizes a gain map.
Figure 17B:
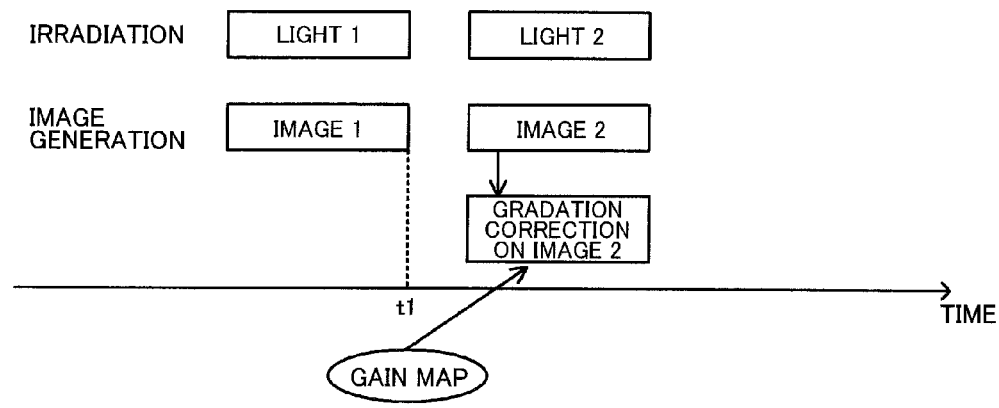
Figure 17C:
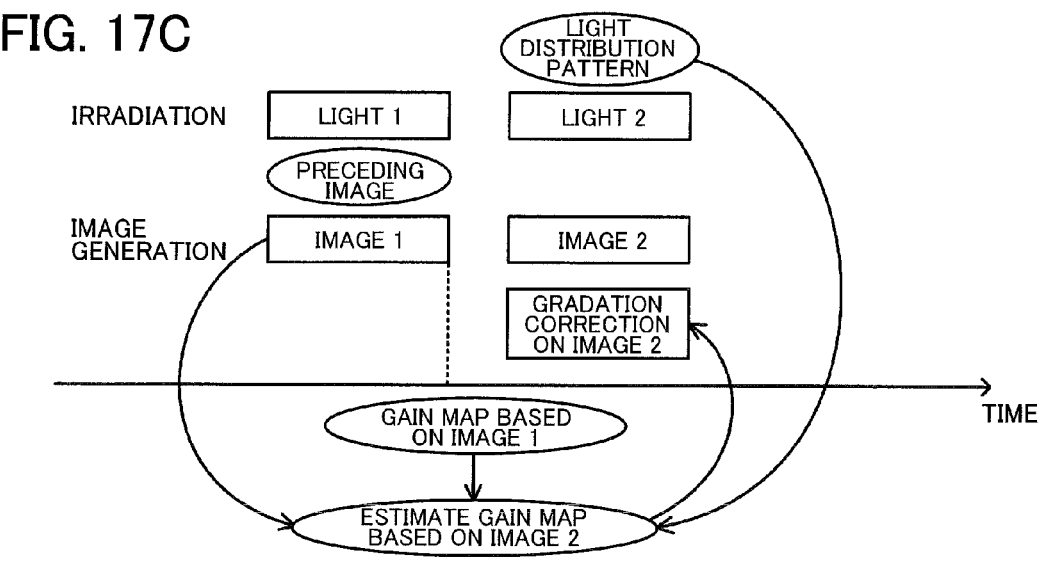

FIGS. 17A to 17C are timing charts illustrating the irradiation timing and the image generation timing. As illustrated in FIG. 17A, when light 1 is applied, and an image 1 is generated (captured), a gain map based on the image 1 is generated after a timing t1 at which the image 1 has been generated. Specifically, the gradation correction process that utilizes the gain map generated based on the image 1 is performed after the timing t1, and an image obtained by the gradation correction process is displayed after a timing t2, for example. Since the image 1 is generated upon application of the light 1, the irradiation timing and the display timing are shifted from each other by one frame in the example illustrated in FIG. 17A.

When it is desired to suppress a frame delay as much as possible, the method illustrated in FIG. 17B may be employed, for example. In FIG. 17B, the gain map that is generated based on the image 1 after the timing t1 is applied to an image 2 that is generated in the subsequent frame. Since the gradation correction process can be performed on the image 2 while generating the image 2 when the gain map has been generated in advance, the image 2 subjected to the gradation correction process can be output with only a small delay from the timing at which application of light 2 has completed. In this case, however, the gain map generated based on the image 1 (i.e., an image in the preceding frame) is applied to the image 2 to which the gain map generated based on the image 2 should be applied. Therefore, it is desirable to use the method illustrated in FIG. 17B when the gain map the based on the image 1 is close to the gain map based on the image 2 (e.g., when the difference between the image 1 and the image 2 is small).

The method illustrated in FIG. 17C may be employed when it is not appropriate to apply the gain map the based on the image 1 to the image 2, for example. In FIG. 17C, a gain map based on the image 2 is estimated using various types of information before acquiring the image 2. The gradation correction process is performed on the image 2 using the estimated gain map. The method illustrated in FIG. 17C can prevent a frame delay in the same manner as the method illustrated in FIG. 17B. The method illustrated in FIG. 17C can implement an accurate gradation correction process as compared with the method illustrated in FIG. 17B when the accuracy of the gain map estimation process is sufficient.

The gain map may be estimated in various ways. For example, a correction process may be performed on the gain map based on the image 1 acquired at the timing t1 using the image 1 (preceding image), and a light distribution pattern (that has been determined before applying the light 2) that determines the light 2 applied when generating the image 2. Alternatively, the gain map may be estimated by a method that predicts a state in which a variation in brightness is not canceled using the light distribution pattern information determined by the light distribution pattern determination section 22. For example, when the end section of the endoscope 1 has a configuration in which the irradiation ports 12a and 12b are provided on either side of the objective lens 16 that corresponds to the imaging section (see FIG. 18A), the captured image illustrated in FIG. 18B is obtained in which each irradiation range (i.e., the range in which the illumination light sufficiently reaches the object) corresponds to each irradiation port, and light does not sufficiently reach the shaded area. It is estimated that the gain value increases in the shaded area.

3.5 Specific Example of Second Embodiment

According to the second embodiment, the endoscope apparatus further includes the noise reduction section 25 that reduces a noise component included in the captured image (see FIG. 15), and the noise reduction section 25 determines at least one of the level of the noise reduction process and the target area of the noise reduction process based on the gain map calculated by the gradation correction section 23 during the gradation correction process.

More specifically, the noise reduction section 25 may perform at least one of a process that increases the level of the noise reduction process performed on an area in which the gain value represented by the gain map is large as compared with the level of the noise reduction process performed on an area in which the gain value is small, and a process that sets the area in which the gain value is large to be the target area of the noise reduction process.

This makes it possible to perform the noise reduction process using the gain map calculated by the gradation correction process. An area in which the gain value represented by the gain map is large has a small signal value (e.g., brightness value), and the amount of noise included in the area increases when the signal value of the area is increased by the gain-up process. Therefore, it is possible to suppress an increase in the amount of noise due to the gain-up process, and provide an image with high visibility by increasing the level of the noise reduction process performed on such an area, or setting such an area to be the target area of the noise reduction process.

The light distribution pattern determination section 22 may determine the light distribution pattern of illumination light based on the gain map calculated by the gradation correction section 23 during the gradation correction process, and the distance information.

More specifically, the light distribution pattern determination section 22 may determine the light distribution pattern that increases the intensity of illumination light applied to an area in which the gain value represented by the gain map is large, as compared with an area in which the gain value is small.

This makes it possible to perform the light distribution pattern determination process using the gain map in addition to the distance information. Since it is likely that the light intensity is insufficient in an area in which the gain value is large, the area can be captured at the correct exposure by determining the light distribution pattern so that the intensity of illumination light applied to the area increases.

The endoscope apparatus may further include the light intensity control section 301 that performs the light intensity control process on the light source that emits illumination light (see FIG. 16), and the light intensity control section 301 may perform the light intensity control process on the light source based on the gain map calculated by the gradation correction section 23 during the gradation correction process.

More specifically, the light intensity control section 301 may perform the light intensity control process that increases the intensity of illumination light emitted from the light source when an area in which the gain value represented by the gain map is larger than a given gain threshold value is larger than a given area threshold value.

The light intensity controlled by the light intensity control section 301 uniformly contributes to the intensity of illumination light applied from the illumination section 14 in each irradiation direction. For example, when employing the configuration illustrated in FIG. 15, the intensity of illumination light applied from each irradiation port 12 is determined by the intensity of illumination light emitted from the light source included in the light source section 4, and the polarization means 13 corresponding to each irradiation port. In this case, the intensity of illumination light applied from each irradiation port 12 uniformly increases when the intensity of illumination light emitted from the light source has been increased. Specifically, the control process performed by the light intensity control section 301 differs in point of view from the light distribution pattern determination process performed by the light distribution pattern determination section 22.

This makes it possible to deal with an area for which the light intensity is estimated to be insufficient by controlling the intensity of illumination light emitted from the light source. However, since the light intensity in each irradiation direction uniformly increases when the intensity of illumination light emitted from the light source is controlled as described above, the brightness of a bright area may increase to a large extent (i.e., blown out highlights may occur in the corresponding area of the captured image). Therefore, it is preferable that the light intensity control section 301 decrease the intensity of illumination light emitted from the light source when blown out highlights have been detected, for example. The light intensity control process that increases the intensity of illumination light emitted from the light source may be performed by comparing the ratio of pixels having a gain value equal to or larger than a given value with a given threshold value, or comparing the maximum gain value with a given threshold value. Note that various other modifications may also be made.

The first embodiment and the second embodiment according to the invention and the modifications thereof have been described above. Note that the invention is not limited thereto. Various modifications and variations may be made of the first embodiment, the second embodiment, and the modifications thereof without departing from the scope of the invention. A plurality of elements described in connection with the first embodiment, the second embodiment, and the modifications thereof may be appropriately combined to implement various configurations. For example, an arbitrary element may be omitted from the elements described in connection with the first embodiment, the second embodiment, and the modifications thereof. Some of the elements described above in connection with different embodiments or modifications thereof may be appropriately combined. Any term cited with a different term having a broader meaning or the same meaning at least once in the specification and the drawings can be replaced by the different term in any place in the specification and the drawings. Specifically, various modifications and applications are possible without materially departing from the novel teachings and advantages of the invention.

What is claimed is:

1. An endoscope apparatus comprising:
   an endoscope comprising:
      an image sensor configured to capture one or more images of an object;
      a light source configured to emit an illumination light; and
      an end section defining an irradiation port through which the illumination light is applied to illuminate the object; and
   a processor comprising hardware, wherein the processor is configured to perform processes comprising:
      acquiring distance information about a distance from the end section of the endoscope to the object;
      determining a light distribution pattern of the illumination light to be applied from the light source based on the distance information;
      performing a gradation correction process on a captured image of the object, under illumination by the illumination light having the light distribution pattern, captured by the image sensor,
      calculating a gain map; and
      determining the light distribution pattern of the illumination light based on the gain map and the distance information.

2. The endoscope apparatus as defined in claim 1,
   wherein the end section defines two or more of the irradiation port, and
   wherein the processor is configured to perform processes comprising:
      determining information that adjusts an intensity of the illumination light applied from each of the two or more of the irradiation port as the light distribution pattern of the illumination light to be applied from the light source based on the distance information.

3. The endoscope apparatus as defined in claim 2,
   wherein the two or more of the irradiation port comprises:
      a first irradiation port through which a first illumination light of the illumination light is applied to illuminate the object, the first illumination light being captured in a first area of the captured image; and
      a second irradiation port through which a second illumination light of the illumination light is applied to illuminate the object, the second illumination light being is captured in a second area of the captured image, the second area differing from the first area, and
   wherein the processor is configured to perform processes comprising:
      determining information that adjusts an intensity of the first illumination light applied from the first irradiation port and an intensity of the second illumination light applied from the second irradiation port as the light distribution pattern of the illumination light to be applied from the light source based on the distance information.

4. The endoscope apparatus as defined in claim 2,
   wherein the two or more of the irradiation port comprises:
      a first irradiation port configured such a first illumination light of the illumination light is applied in a first direction with respect to the image sensor to illuminate the object; and
      a second irradiation port configured such that a second illumination light of the illumination light is applied in a second direction with respect to the image sensor to illuminate the object, the second direction differing from the first direction, and wherein the processor is configured to perform processes comprising:

determining information that adjusts an intensity of the first illumination light applied from the first irradiation port and an intensity of the second illumination light applied from the second irradiation port as the light distribution pattern of the illumination light to be applied from the light source based on the distance information.

5. The endoscope apparatus as defined in claim 1,
wherein the processor is configured to perform processes comprising:

determining at least one of a level of a noise reduction process and a target area of the noise reduction process based on the gain map; and reducing the noise component included in the captured image based on the at least one of the level of the noise reduction process and the target area of the noise reduction process.

6. The endoscope apparatus as defined in claim 5,
wherein the processor is configured to perform processes comprising:

performing at least one of a process that increases the level of the noise reduction process performed on an area in which a gain value represented by the gain map is large as compared with the level of the noise reduction process performed on an area in which the gain value is small, and a process that sets the area in which the gain value is large to be the target area of the noise reduction process.

7. The endoscope apparatus as defined in claim 1,
wherein the processor is configured to perform processes comprising:

determining the light distribution pattern to increase an intensity of the illumination light to be applied to an area in which a gain value represented by the gain map is large, as compared with an area in which the gain value is small.

8. The endoscope apparatus as defined in claim 1,
wherein the processor is configured to perform processes comprising:

controlling a light intensity of the illumination light emitted by the light source based on the gain map.

9. The endoscope apparatus as defined in claim 8,
the processor is configured to perform processes comprising:

controlling the light intensity to increase an intensity of the illumination light emitted from the light source when an area in which a gain value represented by the gain map is larger than a given gain threshold value.

10. The endoscope apparatus as defined in claim 1,
wherein the image sensor is configured to capture a plurality of the images of the object that respectively correspond to a plurality of viewpoints, and wherein the processor is configured to perform processes comprising:

acquiring the distance information based on parallax information obtained from the plurality of the images captured by the image sensor.

11. The endoscope apparatus as defined in claim 1,
wherein the processor is configured to perform processes comprising:

acquiring the distance information from a measurement device configured to measure distance.

12. A method for operating an endoscope apparatus comprising an endoscope comprising: an image sensor configured to capture one or more images of an object; a light source configured to emit an illumination light; and an end section defining an irradiation port through which the illumination light is applied to illuminate the object, the method comprising:

acquiring, by a processor comprising hardware, distance information about a distance from the end section of the endoscope to the object;

determining, by the processor, a light distribution pattern of the illumination light to be applied from the light source based on the distance information;

performing, by the processor, a gradation correction process on a captured image of the object, under illumination by the illumination light having the light distribution pattern, captured by the image sensor;

calculating, by the processor, a gain map; and determining, by the processor, the light distribution pattern of the illumination light based on the gain map and the distance information.

13. The method as defined in claim 12,
wherein the end section defines two or more of the irradiation port, and wherein the method comprises:

determining, by the processor, information that adjusts an intensity of the illumination light applied from each of the two or more of the irradiation port as the light distribution pattern of the illumination light to be applied from the light source based on the distance information.

14. The method as defined in claim 13,
wherein the two or more of the irradiation port comprises:

a first irradiation port through which a first illumination light of the illumination light is applied to illuminate the object, the first illumination light being captured in a first area of the captured image; and a second irradiation port through which a second illumination light of the illumination light is applied to illuminate the object, the second illumination light being captured in a second area of the captured image, the second area differing from the first area, and wherein the method comprises:

determining, by the processor, information that adjusts an intensity of the first illumination light applied from the first irradiation port and an intensity of the second illumination light applied from the second irradiation port as the light distribution pattern of the illumination light to be applied from the light source based on the distance information.

15. The method as defined in claim 13,
wherein the two or more of the irradiation port comprises:

a first irradiation port configured such a first illumination light of the illumination light is applied in a first direction with respect to the image sensor to illuminate the object; and a second irradiation port configured such that a second illumination light of the illumination light is applied in a second direction with respect to the image sensor to illuminate the object, the second direction differing from the first direction, and wherein the method comprises:

determining, by the processor, information that adjusts an intensity of the first illumination light applied from the first irradiation port and an intensity of the second illumination light applied from the second irradiation port as the light distribution pattern of the illumination light to be applied from the light source based on the distance information.

16. The method as defined in claim 12,
wherein the image sensor is configured to capture a plurality of the images of the object that respectively correspond to a plurality of viewpoints, and
wherein the method comprises:
   acquiring, by the processor, the distance information based on parallax information obtained from the plurality of images captured by the image sensor.

17. The method as defined in claim 12,
wherein the method comprises:
   acquiring, by the processor, the distance information from a measurement device configured to measure distance.

18. An endoscope apparatus comprising:
an endoscope comprising:
   an image sensor configured to capture one or more images of an object;
   a light source configured to emit an illumination light; and
   an end section defining an irradiation port through which the illumination light is applied to illuminate the object; and
a processor comprising hardware, wherein the processor is configured to perform processes comprising:
   acquiring distance information about a distance from the end section of the endoscope to the object;
   determining a light distribution pattern of the illumination light to be applied from the light source based on the distance information;
   performing a gradation correction process on a captured image of the object, under illumination by the illumination light having the light distribution pattern, captured by the image sensor;
   calculating a gain map;
   determining at least one of a level of a noise reduction process and a target area of the noise reduction process based on the gain map; and
   reducing the noise component included in the captured image based on the at least one of the level of the noise reduction process and the target area of the noise reduction process.

19. The endoscope apparatus as defined in claim 18,
wherein the end section defines two or more of the irradiation port, and
wherein the processor is configured to perform processes comprising:
   determining information that adjusts an intensity of the illumination light applied from each of the two or more of the irradiation port as the light distribution pattern of the illumination light to be applied from the light source based on the distance information.

20. The endoscope apparatus as defined in claim 18,
wherein the image sensor is configured to capture a plurality of the images of the object that respectively correspond to a plurality of viewpoints, and
wherein the processor is configured to perform processes comprising:
   acquiring the distance information based on parallax information obtained from the plurality of images captured by the image sensor.

21. The endoscope apparatus as defined in claim 18,
wherein the processor is configured to perform processes comprising:
   acquiring the distance information from a measurement device configured to measure distance.

22. An endoscope apparatus comprising:
an endoscope comprising:
   an image sensor configured to capture one or more images of an object;
   a light source configured to emit an illumination light; and
   an end section defining an irradiation port through which the illumination light is applied to illuminate the object; and
a processor comprising hardware, wherein the processor is configured to perform processes comprising:
   acquiring distance information about a distance from the end section of the endoscope to the object;
   determining a light distribution pattern of the illumination light to be applied from the light source based on the distance information;
   performing a gradation correction process on a captured image of the object, under illumination by the illumination light having the light distribution pattern, captured by the image sensor;
   calculating a gain map; and
   controlling a light intensity of the illumination light emitted by the light source based on the gain map.

23. The endoscope apparatus as defined in claim 22,
wherein the end section defines two or more of the irradiation port, and
wherein the processor is configured to perform processes comprising:
   determining information that adjusts an intensity of the illumination light applied from each of the two or more of the irradiation port as the light distribution pattern of the illumination light to be applied from the light source based on the distance information.

24. The endoscope apparatus as defined in claim 22,
wherein the image sensor is configured to capture a plurality of the images of the object that respectively correspond to a plurality of viewpoints, and
wherein the processor is configured to perform processes comprising:
   acquiring the distance information based on parallax information obtained from the plurality of images captured by the image sensor.

25. The endoscope apparatus as defined in claim 22,
wherein the processor is configured to perform processes comprising:
   acquiring the distance information from a measurement device configured to measure distance.

* * * * *